United States Patent
Li

(10) Patent No.: US 9,056,837 B2
(45) Date of Patent: Jun. 16, 2015

(54) HETEROCYCLE COMPOUNDS AND USES THEREOF

(71) Applicant: Intra-Cellular Therapies, Inc., New York, NY (US)

(72) Inventor: Peng Li, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 0 days.

(21) Appl. No.: 13/728,514

(22) Filed: Dec. 27, 2012

(65) Prior Publication Data

US 2013/0123269 A1  May 16, 2013

Related U.S. Application Data

(63) Continuation of application No. 12/663,189, filed as application No. PCT/US2008/007146 on Jun. 6, 2008, now Pat. No. 8,367,686.

(60) Provisional application No. 60/933,828, filed on Jun. 7, 2007.

(51) Int. Cl.
| | |
|---|---|
| A61K 31/4439 | (2006.01) |
| A61K 31/506 | (2006.01) |
| A61K 45/06 | (2006.01) |
| C07D 239/42 | (2006.01) |
| C07D 405/12 | (2006.01) |

(52) U.S. Cl.
CPC .......... *C07D 239/42* (2013.01); *A61K 31/4439* (2013.01); *C07D 405/12* (2013.01); *A61K 31/506* (2013.01); *A61K 45/06* (2013.01)

(58) Field of Classification Search
CPC .. A61K 31/506; A61K 31/4439; A61K 45/06
USPC ....................................................... 514/275
See application file for complete search history.

(56) References Cited

U.S. PATENT DOCUMENTS

| 5,521,184 | A | 5/1996 | Zimmermann |
| 6,596,746 | B1 | 7/2003 | Das et al. |
| 2004/0028673 | A1 | 2/2004 | Netzer et al. |
| 2004/0176395 | A1* | 9/2004 | Flynn et al. .................... 514/256 |
| 2006/0293340 | A1 | 12/2006 | Batt et al. |
| 2010/0120787 | A1 | 5/2010 | Sutcliffe et al. |
| 2010/0173924 | A1 | 7/2010 | Li |
| 2010/0184778 | A1 | 7/2010 | Li |

FOREIGN PATENT DOCUMENTS

| EP | 0 564 409 | 1/2001 |
| EP | 1 533 304 | 5/2005 |
| EP | 1 840 122 | 10/2007 |
| WO | WO 03/057165 | 7/2003 |
| WO | WO 03/062220 | 7/2003 |
| WO | WO 2004/005281 | 1/2004 |
| WO | WO 2004/110452 | 12/2004 |
| WO | WO 2005/039586 | 5/2005 |
| WO | WO 2005/072826 | 11/2005 |
| WO | WO 2006/021458 | 3/2006 |
| WO | WO 2006/069525 | 7/2006 |

OTHER PUBLICATIONS

Youdim, The Path from Anti Parkinson Drug Selegiline and Rasagiline to Multifunctional Neuroprotective Anti Alzheimer Drugs Ladostigil and M30, Current Alzheimer Research, 3, 541-550 (2006).*
Appels et al, "Quantitative analysis of the farnesyl transferase inhibitor lonafarib (Sarasar™, SCH66336) in human plasma using high performance liquid chromatography coupled with tandem mass spectrometry" Rapid Commun. Mass Spectrom (2005) 19: 2187-2192.
Netzer et al, "Gleevec inhibits β-amyloid production but not Notch cleavage" Proc. Nat'l. Acad. Sci. (2003) 100(21) 12444-12449.
Nurden et al. "Platelets, Inflammation and Tissue Regeneration", Thrombosis and Haemostasis Supplement; S13-S33 (2011).
Plant et al, "The production of amyloid beta peptide is a critical requirement for the viability of central neurons" J. Neurosci. (2003) 23(13): 5531-5535.
Youdim, M. "The path from anti Parkinson drug selegiline and rasagiline to multifunctional neuroprotective anti Alzheimer drugs ladostigil and m30" Curr. Alzh.Res. (2006) 3 (5) 541-50.
Zhao et al., "Specific method for determination of gefitinib in human plasma, mouse plasma and tissues using high performance liquid chromatography coupled to tandem mass spectrometry" J. Chromatogr. B. Analyt. Technol. Biomed Life Sci. (2005) 819: 73-80.
Zimmerman et al, "Potent and Selective inhibitors of the ABL-Kinase: phenylamino-pyrimidine (PAP) derivatives" Bioorganic & Medicinal Chem. Lett. (1997), 7(2): 187-192.
International Search Report and Written Opinion of the International Searching Authority for International Application No. PCT/US2008/007167 dated Aug. 18, 2008.
Office Action from the European Patent Office for EP Application No. 08768240.7 dated Sep. 5, 2011.
Office Action from the European Patent Office for EP Application No. 08768240.7 dated Mar. 9, 2012.
Supplementary Search Report from the European Patent Office for EP Application No. 08768240.7.

* cited by examiner

Primary Examiner — Erich A Leeser
(74) Attorney, Agent, or Firm — Hoxie & Associates, LLC

(57) ABSTRACT

The invention relates to chemical compounds, or pharmaceutically acceptable salts thereof of the formula (I):

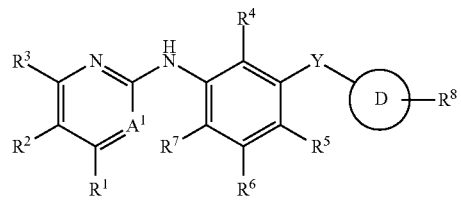

which penetrate the blood brain barrier, inhibit the formation and accumulation of beta-amyloid, and are useful in the treatment of neurodegenerative diseases, particularly Alzheimer's disease. Further, the compounds of the present invention inhibit certain kinases, thereby being useful for the treatment of cancers of the central nervous system.

16 Claims, No Drawings

HETEROCYCLE COMPOUNDS AND USES THEREOF

CROSS REFERENCE TO RELATED APPLICATIONS

This application is a continuation application of U.S. application Ser. No. 12/663,189 filed Dec. 4, 2009, which is a US filing under 35 USC 371 of PCT/US2008/007146 filed on Jun. 6, 2008, which claims the benefit of provisional application 60/933,828 filed on Jun. 7, 2007 the contents of each of which are incorporated herein by reference.

FIELD OF THE INVENTION

The present invention relates to novel heterocycles, their pharmaceutical compositions and methods of use. In addition, the present invention relates to therapeutic methods that penetrate the blood-brain barrier and inhibit the formation and accumulation of beta-amyloid. Accordingly, the compounds and compositions of the present invention are useful in the treatment of neurodegenerative diseases, particularly Alzheimer's disease. Further, the compounds of the present invention inhibit certain kinases, thereby being useful for the treatment of cancers of the central nervous system.

BACKGROUND OF THE INVENTION

Without being bound to theory, it is believed that the pathology of Alzheimer's disease ("AD") involves amyloid-β ("Aβ") peptides, which are metabolites of β-amyloid precursor protein (Alzheimer's disease-associated precursor protein or "APP"), and are believed to be major pathological determinants of AD. These peptides consist mainly of 40 to 42 amino acids, Aβ1-40 ("Aβ40") and Aβ1-42 ("Aβ42"), respectively. Aβ40 and Aβ42 are generated by two enzymatic cleavages occurring close to the C-terminus of APP. The enzymes responsible for the cleavage, β-secretase and γ-secretase, generate the N- and C-termini of Aβ, respectively. The amino terminus of Aβ is formed by β-secretase cleavage between methionine residue 596 and aspartate residue 597 of APP (numbering based on APP 695 isoform). γ-secretase cleaves at varying positions 38-, 40- or 43-residues C-terminal of this β-secretase cleavage product to release the Aβ peptides. A third enzyme, α-secretase, cleaves the precursor protein between the Aβ- and γ-cleavage sites, thus precluding Aβ production and releasing an approximately 3 kDa peptide known as P3, which is non-pathological. Both β- and α-secretase cleavage also result in soluble, secreted-terminal fragments of APP, known as sAPPβ and sAPPα, respectively. The sAPPα fragment has been suggested to be neuroprotective. These secretases may also be involved in the processing of other important proteins. For example, γ-secretase also cleaves Notch-1 protein.

A drug which selectively inhibits Aβ formation and/or accumulation is thus of potential interest for the treatment, management and prevention of Alzheimer's disease. To maximize utility, however, it is also desirable that it can be readily delivered to relevant site of action in the brain. Brain is protected from chemical insult by a selective barrier, referred to as the blood-brain barrier ("BBB"), that many drug-like compounds are unable to penetrate.

International Patent Publication No. WO 03/057165 discloses that certain previously known inhibitors of tyrosine kinases are useful to inhibit the production of and accumulation of Aβ. Such compounds included those described in U.S. Pat. No. 5,521,184, which includes imatinib. Netzer et al., Proc Natl Acad. Sci., 100(21):12444-9 (2003) showed that imatinib inhibits production of Aβ without affecting γ-secretase cleavage of Notch-1 and without unacceptable toxicity to the neurons. A major disadvantage with using imatinib for the treatment or prevention of Alzheimer's disease, however, is that penetration of this compound across the BBB is poor because imatinib is actively pumped out of the brain by a P-glycoprotein system, thereby preventing high concentrations of the compound from accumulating in the brain. Accordingly, imatinib is generally not used for the treatment of cancers of the central nervous system.

International Patent Publication No. WO 05/072826 describes compositions and methods of use for tyrosine kinase inhibitors to treat pathogenic infection. J. Zimmermann et al., Bioorganic & Medicinal Chem. Lett., 7(2):187-192 describes potent and selective inhibitors of the ABL-kinase: phenylamino-pyrimidine (PAP) derivatives. International Patent Publication No. EP 1 533 304 describes amide derivatives. International Patent Publication No. WO 04/005281 describes inhibitors of tyrosine kinases. International Patent Publication No. WO 05/039586 describes the use of pyridinyl-pyrimidinylamino-benzamide derivatives for the treatment of amyloid related disorders. U.S. Pat. No. 5,521,184 describes pyrimidine derivatives and processes for the preparation thereof. International Patent Publication WO 04/110452 describes substituted phenyl compounds.

SUMMARY OF THE INVENTION

The present invention is directed to compounds of formula (I):

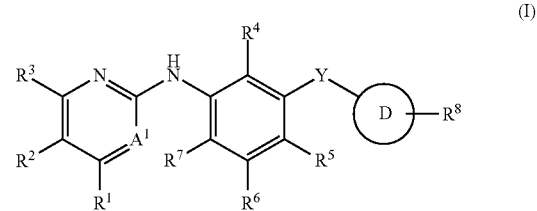

which penetrate the blood-brain barrier, inhibit the formation and accumulation of beta-amyloid, and are useful in the treatment of neurodegenerative diseases, particularly Alzheimer's disease. Further, the compounds of the present invention inhibit certain kinases, thereby being useful for the treatment of cancers of the central nervous system.

DETAILED DESCRIPTION OF THE INVENTION

The compounds of the present invention are represented by formula (I):

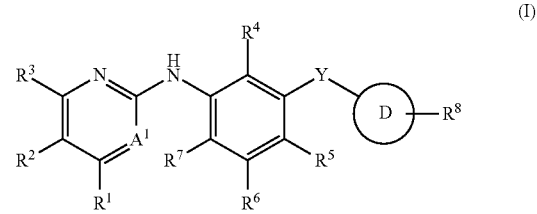

in free or salt form, wherein:
$A^1$ is CH or N;
$R^1$ is $C_{1-6}$alkyl, $C_{1-6}$cycloalkyl, or aryl optionally substituted with alkyl, haloalkyl, alkyloxy, or halo group;
$R^2$, $R^3$, $R^4$, $R^5$, $R^6$ and $R^7$ are independently hydrogen, halo, $C_{1-4}$alkyl, $C_{1-4}$alkyloxy, or trifluoromethyl;

or R$^5$ and R$^6$, together with carbon atoms to which they are attached, form a 5 or 6 member hetcyclic ring;

Y is —NHCO—, —CONH—, —NHSO$_2$—, —NH-CONH—, or —NHCH$_2$—;

D is a 5 or 6 membered aryl, hetaryl, or hetcyclic ring having at least one N, S, or O ring atom, or a C ring atom forming an oxo(C═O) moiety; provided that D is not a substituted phenyl group if A$^1$═N and R$^2$═R$^3$═R$^4$═R$^5$═R$^6$═H and R$^7$═CH$_3$ and Y═NHCO; and R$^8$ is C$_{0-6}$alkyl, C$_{3-7}$cycloalkyl, aryl, hetaryl, aryl(C$_{1-4}$alkyl)-, hetcyclyl(C$_{0-4}$alkyl)-, or —C$_{0-6}$alkyl-N(C$_{0-6}$alkyl)(C$_{0-6}$alkyl), optionally substituted with C$_{1-6}$alkyl.

In one aspect, the compounds of the present invention are represented by Formula I in free or salt form, wherein Y is —NHCO— and the other variables are as defined above for Formula I.

In an embodiment of this aspect, the compounds of the present invention are represented by Formula I in free or salt form, wherein Y is —NHCO—; A$^1$ is N; and the other variables are as defined above for Formula I.

In a second aspect, the compounds of the present invention are represented by Formula I in free or salt form, wherein Y is —CONN— and the other variables are as defined above for Formula I.

In an embodiment of the second aspect, the compounds of the present invention are represented by Formula I in free or salt form, wherein Y is —CONH—; A$^1$ is N; and the other variables are as defined above for Formula I.

In another embodiment of the second aspect, the compounds of the present invention are represented by Formula I in free or salt form, wherein Y is —CONN—; A$^1$ is N; R$^5$ and R$^6$, together with carbon atoms to which they are attached, form a 5 or 6 member hetcyclic ring; and the other variables are as defined above for Formula I.

In another embodiment of the second aspect, the compounds of the present invention are represented by Formula I in free or salt form, wherein Y is —CONH—; A$^1$ is C; and the other variables are as defined above for Formula I.

In a third aspect, the compounds of the present invention are represented by Formula I in free or salt form, wherein Y is —NHSO$_2$— and the other variables are as defined above for Formula I.

In a fourth aspect, the compounds of the present invention are represented by Formula I in free or salt form, wherein Y is —NHCONH— and the other variables are as defined above for Formula I.

In a fifth aspect, the compounds of the present invention are represented by Formula I in free or salt form, wherein Y is —NHCH$_2$— and the other variables are as defined above for Formula I.

In another aspect of the present invention, compounds of the invention are selected from the following compounds:

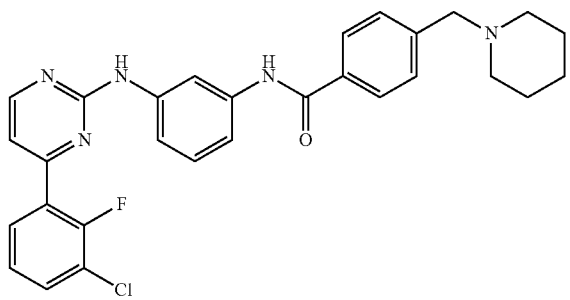 [SMILES: O=C(Nc1cccc(Nc2nccc(-c3cccc(Cl)c3F)n2)c1)c1ccc(CN2CCCCC2)cc1]

-continued

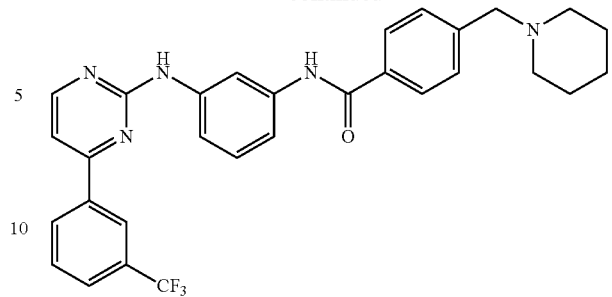

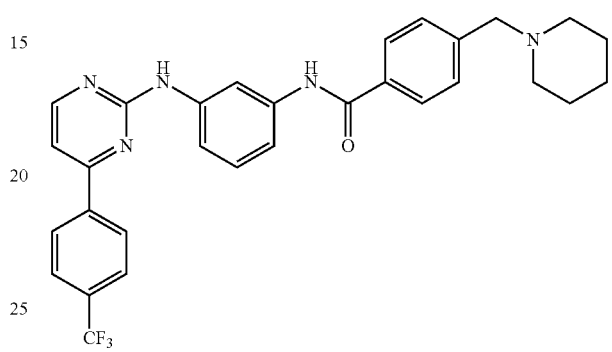

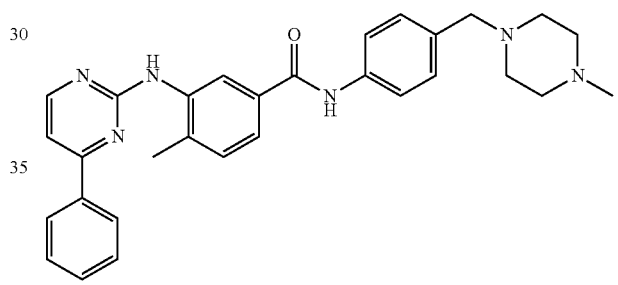

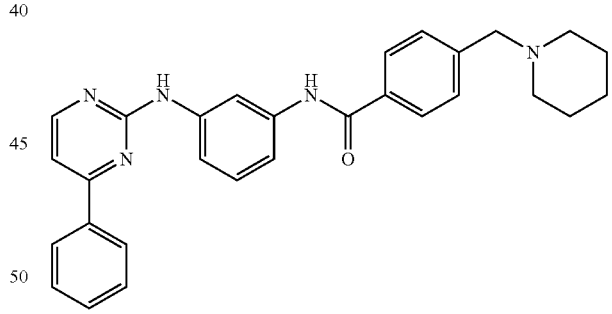

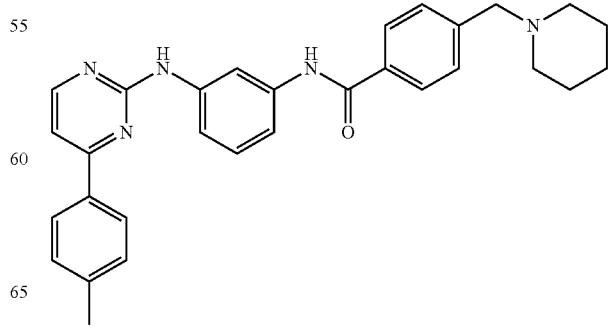

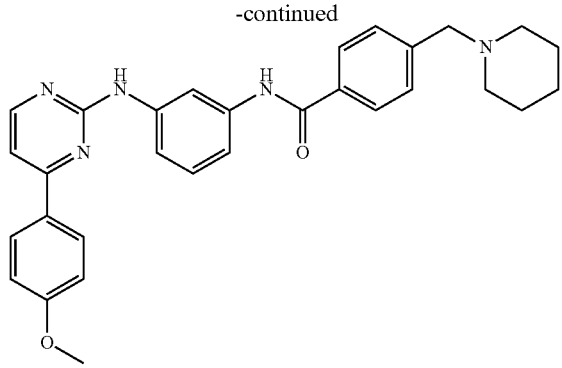
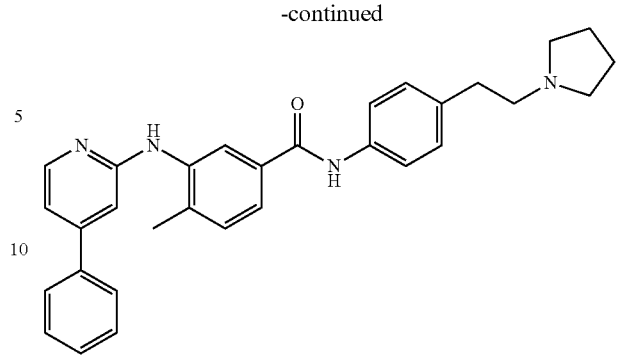
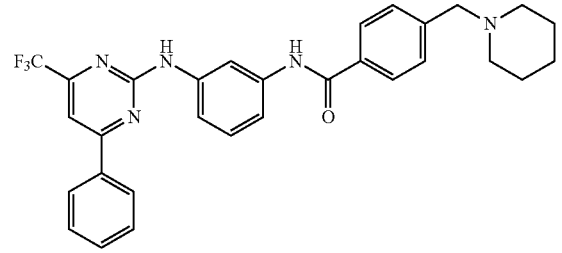
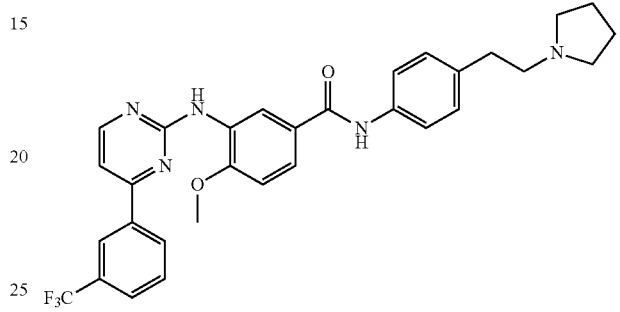
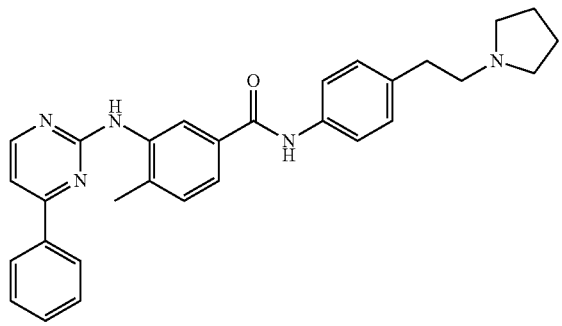
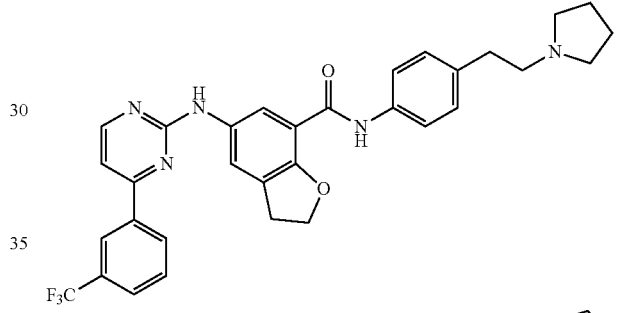
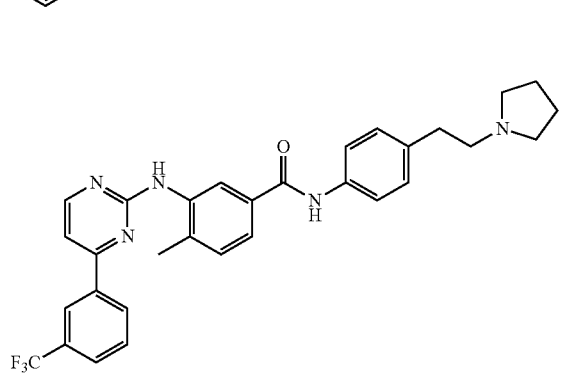
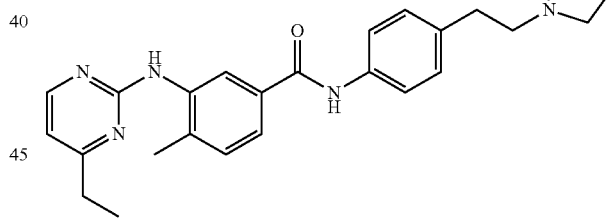
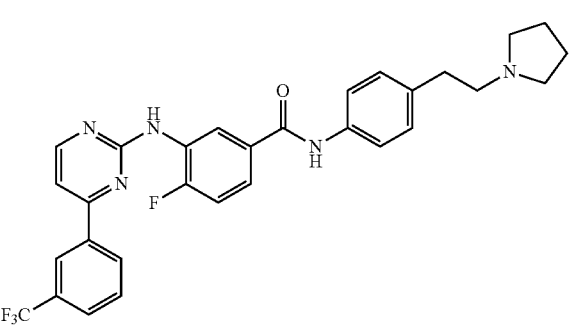

in free or salt form.

Therefore, the invention provides the following:
1.1 a Compound of Formula I, wherein $A^1$ is CH or N;
1.2 a Compound of Formula I or 1.1, wherein $A^1$ is CH;
1.3 a Compound of Formula I or 1.1, wherein $A^1$ is N,
1.4 a Compound of Formula I or 1.1, 1.2 or 1.3, wherein $R^1$ is $C_{1-6}$alkyl, $C_{1-6}$cycloalkyl, or aryl optionally substituted with alkyl, haloalkyl, alkyloxy, or halo group;
1.5 a Compound of Formula I or any of 1.1-1.4, wherein $R^1$ is aryl optionally substituted with alkyl, haloalkyl, alkyloxy, or halo group;
1.6 a Compound of Formula I or any of 1.1-1.5, wherein $R^1$ is aryl;
1.7 a Compound of Formula I or any of 1.1-1.6, wherein $R^1$ is phenyl;
1.8 a Compound of Formula I or any of 1.1-1.5, wherein $R^1$ is phenyl optionally substituted with alkyl, haloalkyl, alkyloxy, or halo group;

1.9 a Compound of Formula I or any of 1.1-1.5, wherein $R^1$ is aryl optionally substituted with halo (e.g., chloro, fluoro);

1.10 a Compound of Formula I or any of 1.1-1.5 or 1.9, wherein $R^1$ is phenyl optionally substituted with halo (e.g., chloro, fluoro);

1.11 a Compound of Formula I or any of 1.1-1.5 or 1.9-1.10, wherein $R^1$ is phenyl optionally substituted with chloro and fluoro;

1.12 a Compound of Formula I or any of 1.1-1.5 or 1.9-1.11, wherein $R^1$ is 3-chloro-2-fluorophenyl;

1.13 a Compound of Formula I or any of 1.1-1.5, wherein $R^1$ is aryl optionally substituted with haloalkyl (e.g., trifluoromethyl);

1.14 a Compound of Formula I or any of 1.1-1.5 or 1.13, wherein $R^1$ is phenyl optionally substituted with haloalkyl (e.g., trifluoromethyl);

1.15 a Compound of Formula I or any of 1.1-1.5 or 1.13-1.14, wherein $R^1$ is phenyl optionally substituted with trifluoromethyl;

1.16 a Compound of Formula I or any of 1.1-1.5 or 1.13-1.15, wherein $R^1$ is 4-trifluoromethylphenyl;

1.17 a Compound of Formula I or any of 1.1-1.5 or 1.13-1.15, wherein $R^1$ is 3-trifluoromethylphenyl;

1.18 a Compound of Formula I or any of 1.1-1.5, wherein $R^1$ is aryl optionally substituted with alkyl (e.g., methyl);

1.19 a Compound of Formula I or any of 1.1-1.5 or 1.18, wherein $R^1$ is phenyl optionally substituted with alkyl (e.g., methyl);

1.20 a Compound of Formula I or any of 1.1-1.5 or 1.18-1.19, wherein $R^1$ is phenyl optionally substituted with methyl;

1.21 a Compound of Formula I or any of 1.1-1.5 or 1.18-1.20 wherein $R^1$ is 4-methylphenyl;

1.22 a Compound of Formula I or any of 1.1-1.5 wherein $R^1$ is aryl optionally substituted with alkoxy (e.g., methoxy);

1.23 a Compound of Formula I or any of 1.1-1.5 or 1.22 wherein $R^1$ is phenyl optionally substituted with alkoxy (e.g., methoxy);

1.24 a Compound of Formula I or any of 1.1-1.5 or 1.22-1.23 wherein $R^1$ is 4-methoxyphenyl;

1.25 a Compound of Formula I or any of 1.1-1.4, wherein $R^1$ is $C_{1-6}$alkyl (e.g., ethyl);

1.26 a Compound of Formula I or any of 1.1-1.4 or 1.25, wherein $R^1$ is ethyl;

1.27 a Compound of Formula I or any of 1.1-1.26, wherein $R^2$, $R^3$, $R^4$, $R^5$, $R^6$ and $R^7$ are independently hydrogen, halo, $C_{1-4}$alkyl, $C_{1-4}$alkyloxy, or trifluoromethyl;

1.28 a Compound of Formula I or any of 1.1-1.27, wherein any of $R^2$ is hydrogen;

1.29 a Compound of Formula I or any of 1.1-1.28, wherein $R^3$ is trifluoromethyl;

1.30 a Compound of Formula I or any of 1.1-1.28, wherein $R^3$ is hydrogen;

1.31 a Compound of Formula I or any of 1.1-1.30, wherein $R^4$ is hydrogen;

1.32 a Compound of Formula I or any of 1.1-1.31, wherein $R^5$ is hydrogen;

1.33 a Compound of Formula I or any of 1.1-1.32, wherein $R^6$ is hydrogen;

1.34 a Compound of Formula I or any of 1.1-1.31, wherein $R^5$ and $R^6$, together with carbon atoms to which they are attached, form a 5 or 6 member hetcyclic ring;

1.35 a Compound of Formula I or any of 1.1-1.31 or 1.34, wherein $R^5$ and $R^6$, together with carbon atoms to which they are attached, form a 5-member hetcyclic ring;

1.36 a Compound of Formula I or any of 1.1-1.31 or 1.34-1.35, wherein $R^5$ and $R^6$, together with carbon atoms to which they are attached, form a tetrahydrofuran;

1.37 a Compound of Formula I or any of 1.1-1.36, wherein $R^7$ is $C_{1-4}$alkyl (e.g., methyl);

1.38 a Compound of Formula I or any of 1.1-1.37, wherein $R^7$ is methyl;

1.39 a Compound of Formula I or any of 1.1-1.36, wherein $R^7$ is halo;

1.40 a Compound of Formula I or any of 1.1-1.36 or 1.39, wherein $R^7$ is fluoro;

1.41 a Compound of Formula I or any of 1.1-1.36, wherein $R^7$ is hydrogen;

1.42 any of the foregoing compound wherein Y is —NHCO—, —CONH—, —NHSO$_2$—, —NHCONH—, or —NHCH$_2$—;

1.43 a Compound of Formula I or any of 1.1-1.42, wherein Y is —NHCO—;

1.44 a Compound of Formula I or any of 1.1-1.42, wherein Y is —CONH—;

1.45 any of the foregoing formulae wherein D is a 5 or 6 membered aryl, hetaryl, or hetcyclic ring having at least one N, S, or O ring atom, or a C ring atom forming an oxo(C=O) moiety; provided that D is not a substituted phenyl group if $A^1$=N and $R^2$=$R^3$=$R^4$=$R^5$=$R^6$=H and $R^7$=CH$_3$ and Y=NHCO;

1.46 a Compound of Formula I or any of 1.1-1.45, wherein D is aryl;

1.47 a Compound of Formula I or any of 1.1-1.46, wherein D is phenyl;

1.48 any of the foregoing formulae, wherein $R^8$ is $C_{0-6}$alkyl, $C_{3-7}$cycloalkyl, aryl, hetaryl, hetcyclyl ($C_{0-4}$alkyl)-, or —$C_{0-6}$alkyl-N($C_{0-6}$alkyl)($C_{0-6}$alkyl), optionally substituted with $C_{1-6}$alkyl;

1.49 any of the foregoing formulae, wherein $R^8$ is hetcyclyl ($C_{0-4}$alkyl)- optionally substituted with $C_{1-6}$alkyl;

1.50 any of the foregoing formulae, wherein $R^8$ is piperidin-1-ylmethyl or (pyrrolidin-1-yl)ethyl;

1.51 a Compound of Formula I or any of 1.1-1.49, wherein $R^8$ is (piperazin-1-yl)methyl optionally substituted with $C_{1-6}$alkyl;

1.52 Compound of Formula I or any of 1.1-1.49 or 1.51, wherein $R^8$ is (piperazin-1-yl)methyl optionally substituted with methyl;

1.53 Compound of Formula I or any of 1.1-1.49 or 1.52, wherein $R^8$ is 4-methyl(piperazin-1-yl)methyl;

1.54 any of the foregoing compounds selected from the following:

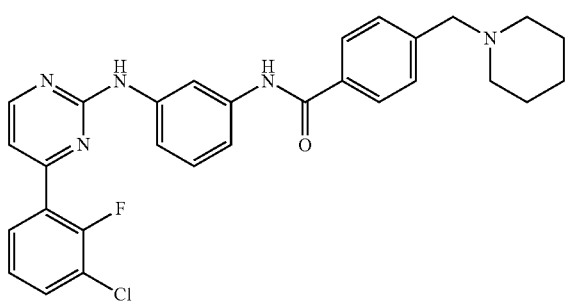

9
-continued
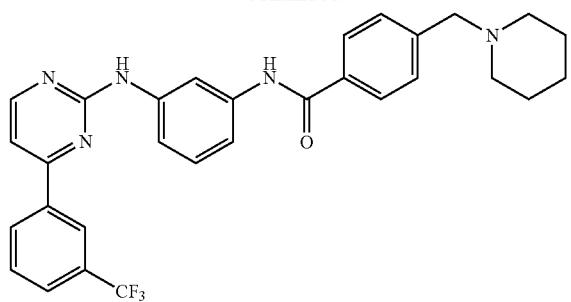 [SMILES: O=C(Nc1cccc(Nc2nccc(-c3cccc(C(F)(F)F)c3)n2)c1)c1ccc(CN2CCCCC2)cc1]
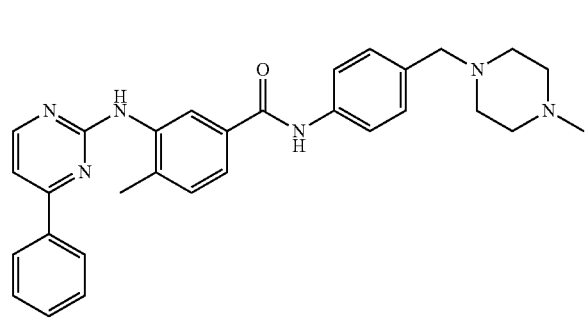 [SMILES: Cc1ccc(C(=O)Nc2ccc(CN3CCN(C)CC3)cc2)cc1Nc1nccc(-c2ccccc2)n1]
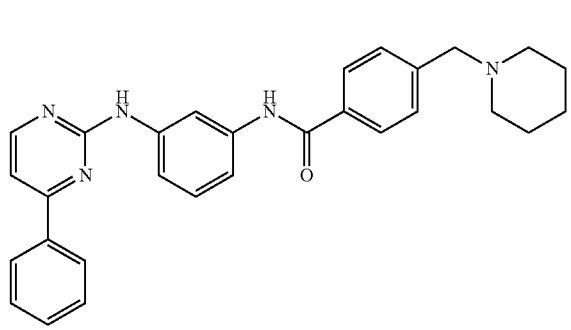 [SMILES: O=C(Nc1cccc(Nc2nccc(-c3ccccc3)n2)c1)c1ccc(CN2CCCCC2)cc1]
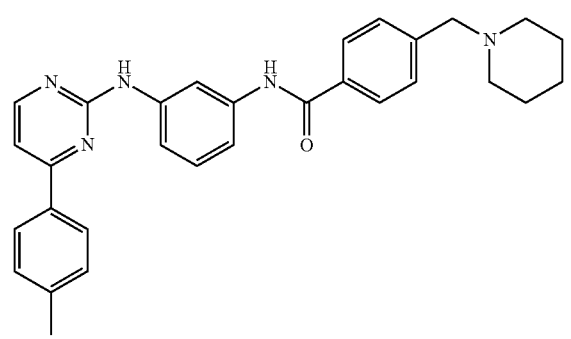 [SMILES: Cc1ccc(-c2ccnc(Nc3cccc(NC(=O)c4ccc(CN5CCCCC5)cc4)c3)n2)cc1]
10
-continued
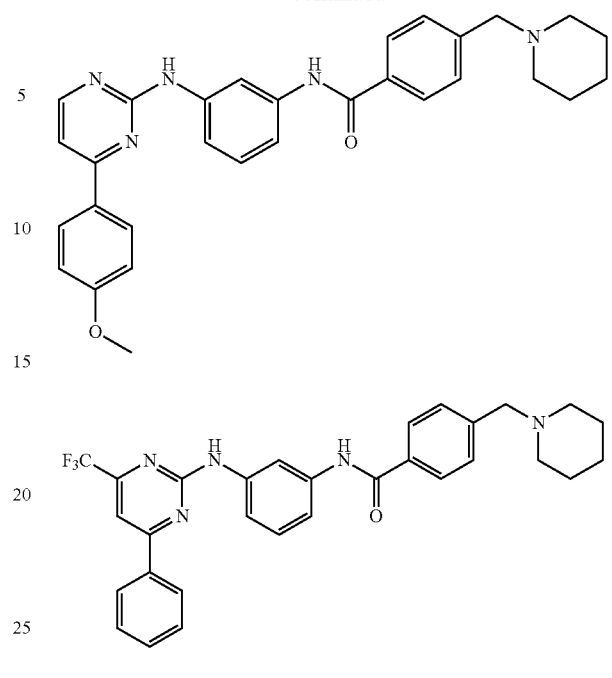
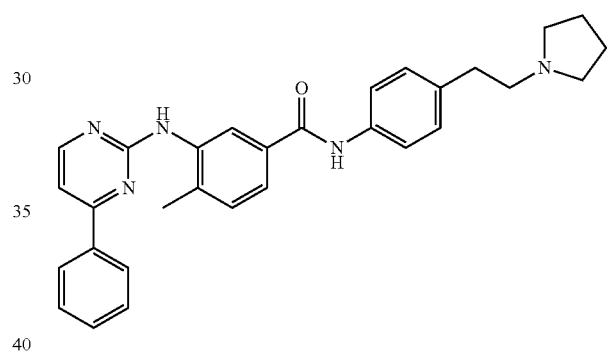
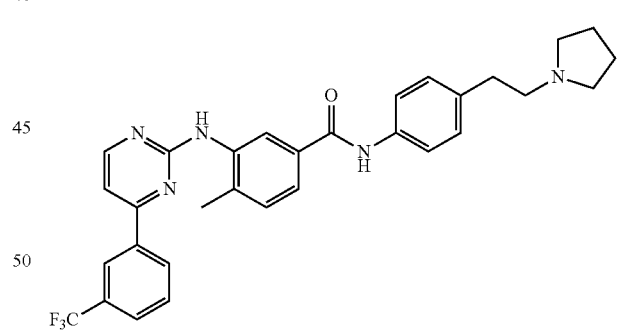
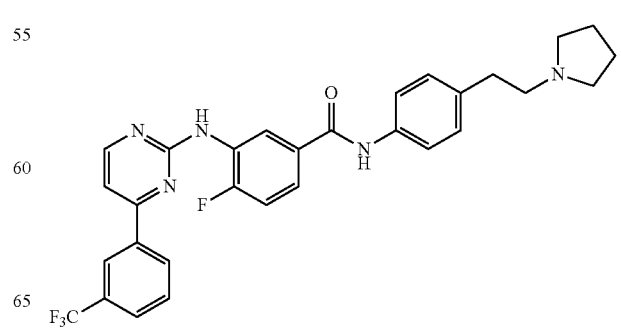

-continued

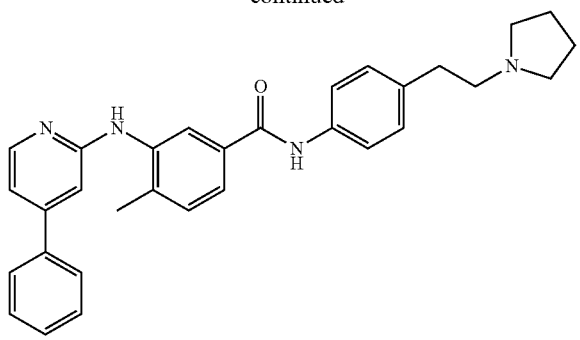

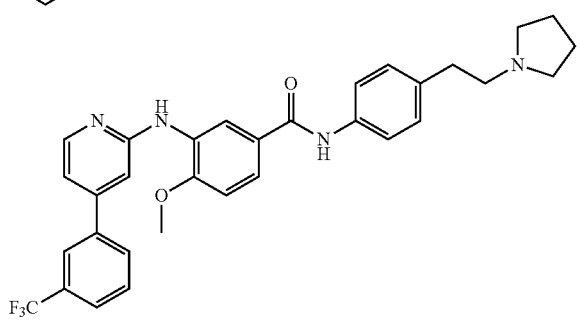

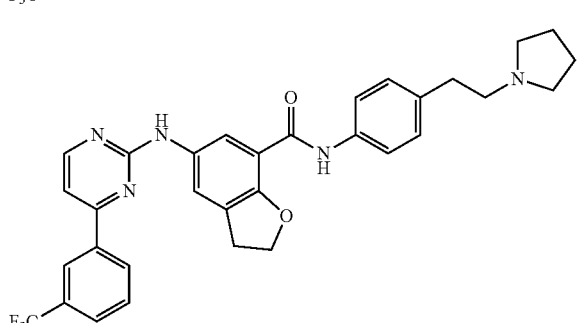

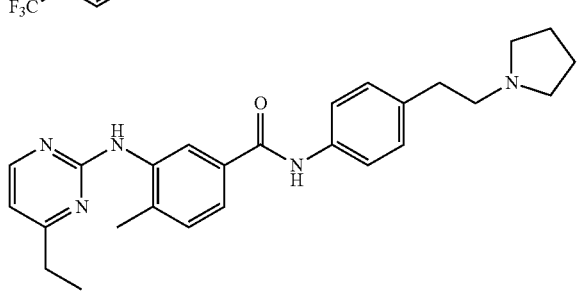

1.55 Any of the foregoing compounds wherein said compound is:

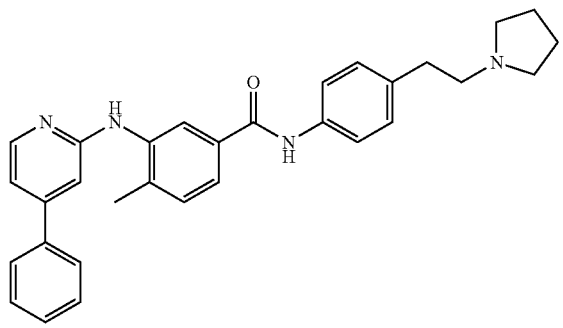

1.56 Any of the foregoing compounds wherein said compound is:

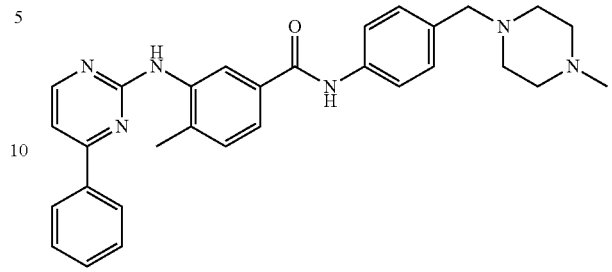

in free or salt form.

The term "alkyl" includes both straight and branched chain alkyl groups. References to individual alkyl groups such as "propyl" are specific for the straight chain version only and references to individual branched chain alkyl groups such as 'isopropyl' are specific for the branched chain version only. For example, "$C_{1-6}$alkyl" includes $C_1$ alkyl, $C_{1-3}$alkyl, propyl, isopropyl and t-butyl. A similar convention applies to other radicals, for example "phenyl$C_{1-6}$alkyl" includes phenyl$C_{1-4}$alkyl, benzyl, 1-phenylethyl and 2-phenylethyl. "$C_0$alkyl" refers to a hydrogen terminus when the $C_0$alkyl is terminal and refers to a direct bond when the "$C_0$alkyl" is bridging (linking). The term "$C_{0-6}$alkyl", for example, refers to adding "$C_0$alkyl" to the scope of the "$C_1$ alkyl" definition. Thus, it is understood that substituents allowed for "$C_{1-6}$alkyl" would accordingly be allowed for the "$C_{1-6}$alkyl" within the scope of "$C_{0-6}$alkyl".

The term "halo" refers to fluoro, chloro, bromo and iodo.

Where optional substituents are chosen from, for example, "1-5 independent" substituents from a list of substituents, it is to be understood that this definition includes all substituents being chosen from one of the specified groups or the substituents being chosen from two or more of the specified groups in the list. Where a substituent is recited using the molecule (parent) name, it is understood that the substituent is the radical of such molecular parent.

An "aryl" is well understood by one in the art and includes phenyl and naphthyl.

A "hetaryl" is a 4-12 membered fully unsaturated or partially unsaturated heterocyclic mono or bicyclic ring containing at least one nitrogen, sulphur or oxygen ring atom and in which, unless otherwise specified, a —$CH_2$— group can optionally be replaced by a —C(O)—. Examples of such hetaryl include indolyl, pyridyl, furyl, thienyl, pyranyl, pyrrolyl, pyrazolyl, isothiazolyl, isobenzofuranyl, 2,3-dihydrobenzofuranyl, imidazo[1,2-a]pyridinyl, benzimidazolyl quinolyl, pyrrolinyl, imidazolyl, pyrimidyl, pyrazinyl, pyridazinyl, isoxazolyl, benzoxazolyl, benzoxazol-2-one, benzopyridazin-dione, pyridine-N-oxide, and quinoline-N-oxide.

A "hetcyclyl" is a saturated, mono or bicyclic ring containing 4-12 atoms containing at least one nitrogen, sulphur or oxygen ring atom. Examples of such "hetcyclyl" include pyrrolidinyl, imidazolidinyl, pyrazolininyl, tetrahydropyranyl, morpholino, piperidyl, and piperazinyl.

Examples of "$C_{1-6}$alkoxy" include methoxy, ethoxy and propoxy.

Examples of "—($C_{0-6}$alkyl)-N($C_{0-6}$alkyl)($C_{0-6}$alkyl)" include methylamino, ethylamino, di-N-methylamino, di-(N-ethyl)amino, and N-ethyl-N-methylamino.

A suitable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

It is also to be understood that certain compounds of the formula (I), e.g., any of 1.1-1.56, can exist in solvated as well as unsolvated forms such as, for example, hydrated forms. It is to be understood that the invention encompasses all such solvated forms which inhibit the formation and accumulation of beta-amyloid.

Particular values of variable groups are as follows. Such values may be used where appropriate with any of the definitions, claims or embodiments defined hereinbefore or hereinafter. According to a further aspect of the invention there is provided a pharmaceutical composition which comprises a compound of the formula (I), e.g., any of 1.1-1.56, in free or pharmaceutically acceptable salt thereof, as defined hereinbefore, in association with a pharmaceutically acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) e.g., any of 1.1-1.56, will normally be administered to a warm-blooded animal at a unit dose within the range 1-1000 mg/kg, and this normally provides a therapeutically-effective dose. Preferably a daily dose in the range of 10-100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), e.g., any of 1.1-1.56, in free or pharmaceutically acceptable salt thereof, as defined hereinbefore for use in a method of treatment of the human or animal body by therapy.

We have found that the compounds defined in the present invention, or a pharmaceutically acceptable salt thereof, can penetrate the blood-brain barrier and inhibit the formation and accumulation of beta-amyloid. Accordingly the compounds of the present invention are useful in the treatment of neurodegenerative diseases, particularly Alzheimer's disease.

We have found that the compounds defined in the present invention, or a pharmaceutically acceptable salt thereof, can inhibit certain kinases. Accordingly the compounds of the present invention are useful in the treatment of cancers of the central nervous system.

Thus according to this aspect of the invention there is provided a compound of the formula (I), e.g., any of 1.1-1.56, in free or pharmaceutically acceptable salt thereof, as defined hereinbefore for use as a medicament.

According to a further aspect of the invention there is provided the use of a compound of the formula (I), e.g., any of 1.1-1.56, in free or pharmaceutically acceptable salt thereof, as defined hereinbefore in the manufacture of a medicament for use in the inhibition of the formation and accumulation of beta-amyloid in a warm-blooded animal such as man.

According to an aspect of the invention there is provided the use of a compound of the formula (I), e.g., any of 1.1-1.56, in free or pharmaceutically acceptable salt thereof, as defined hereinbefore in the manufacture of a medicament for use in the production of an inhibition of certain kinases across the blood-brain barrier in a warm-blooded animal such as man.

According to a further feature of the invention, there is provided the use of a compound of the formula (I), e.g., any of 1.1-1.56, in free or salt form, as defined herein before in the manufacture of a medicament for use in the treatment of cancers of the nervous system and the brain.

According to a further feature of this aspect of the invention there is provided a method for producing an inhibitory effect against the accumulation of abnormal protein aggregates in a warm-blooded animal, such as man, in need of such treatment which comprises administering to said animal an effective amount of a compound of formula (I), e.g., any of 1.1-1.56, in free or pharmaceutically acceptable salt form.

Furthermore, the compounds of this invention, e.g., compound of formula (I) or any of 1.1-1.56, in free or pharmaceutically acceptable salt form, are useful in the treatment, control and management of diseases characterized by accumulation of abnormal protein aggregates, especially in the brain—for example, diseases such as Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins such as A$\beta$. Such abnormal protein aggregates include, for example, i) amyloid plaques and neurofibrillary tangles, and ii) precipitates of tau or amyloid proteins such as A$\beta$.

Accordingly, the present invention provides methods of treatment of Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as A$\beta$. Such method comprises administering to a patient in need thereof an effective amount of a compound of formula (I), e.g., any of 1.1-1.56, in free or pharmaceutically acceptable salt form.

Additionally, the present invention provides methods of treatment of hyperproliferative diseases, especially cancers of the brain or central nervous system, including astrocytoma, medulloblastoma, oligdendroglioma, glioblastoma, glioma, ependymoma, meningioma, sarcoma, germ cell tumor, pinealoma, craniopharyngioma, and pituitary adenoma. Such method comprises administering to a patient in need thereof an effective amount of a compound of formula (I), e.g., any of 1.1-1.56, in free or pharmaceutically acceptable salt form.

The present invention also provides methods of treatment of disease characterized by dysfunctional expression or activity of kinases such as the c-Ab1, BCR-Ab1, ARG, c-Src, c-Kit, FAK, Trk, EGFR, VEGFR, Tie-2, c-Met, FGFR-1, Flt-1, Her-2, c-Raf, PDGFR, PDGFR-beta, MAPK, PKA, PKC, PKCα, PKCδ, CDK5, GSK-3, or JNK, especially overexpression or over-activity of kinases in CNS cells, comprising the administration of an effective amount of a compound or composition of the present invention in free or salt form to a human or animal patient in need thereof. The compound or composition of the present invention useful for the methods of the present methods include a compound of formula (I), e.g., any of 1.1-1.56, in free or pharmaceutically acceptable salt form.

In a further aspect of the invention there is provided a pharmaceutical composition which comprises a compound of the formula (I), e.g., any of 1.1-1.56, in free or pharmaceutically acceptable salt form, as defined herein before in association with a pharmaceutically-acceptable diluent or carrier for use in the treatment, control and management of diseases characterized by accumulation of abnormal protein aggregates, especially in the brain, such as Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins such as Aβ. Such abnormal protein aggregates include, for example, i) amyloid plaques and neurofibrillary tangles, and ii) precipitates of tau or amyloid proteins such as Aβ.

In a further aspect of the invention there is provided a pharmaceutical composition which comprises a compound of the formula (I), e.g., any of 1.1-1.56, in free or pharmaceutically acceptable salt thereof, as defined herein before in association with a pharmaceutically-acceptable diluent or carrier for use in the treatment of Alzheimer's disease, progressive supranuclear palsy, Down Syndrome, memory and cognitive disorders, dementia, amylois neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as Aβ.

The treatment methods include administering the compounds of the present invention, e.g., any of 1.1-1.56, in free or salt form, together with other therapeutic compounds to treat Alzheimer's disease, progressive supranuclear palsy, Down Syndrome, memory and cognitive disorders, dementia, amylois neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as Aβ.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

In addition to their use in therapeutic medicine, the compounds of formula (I) e.g., any of 1.1-1.56, and their pharmaceutically acceptable salts are also useful as pharmacological tools in the development and standardisation of in vitro and in vivo test systems for the evaluation of the effects of inhibitors of accumulation of abnormal protein aggregates, especially in the brain, as part of the search for new therapeutic agents.

In a further aspect of the invention there is provided a pharmaceutical composition which comprises a compound of the formula (I), e.g., any of 1.1-1.56, in free or pharmaceutically acceptable salt thereof, as defined herein before in association with a pharmaceutically-acceptable diluent or carrier for use in the of treatment of hyperproliferative diseases, especially cancers of the brain or central nervous system, including astrocytoma, medulloblastoma, oligdendroglioma, glioblastoma, glioma, ependymoma, meningioma, sarcoma, germ cell tumor, pinealoma, craniopharyngioma, and pituitary adenoma.

In a further aspect of the invention there is provided a pharmaceutical composition which comprises a compound of the formula (I), e.g., any of 1.1-1.56, in free or pharmaceutically acceptable salt thereof, as defined herein before in association with a pharmaceutically-acceptable diluent or carrier for use in the treatment of astrocytoma, medulloblastoma, oligdendroglioma, glioblastoma, glioma, ependymoma, meningioma, sarcoma, germ cell tumor, pinealoma, craniopharyngioma, and pituitary adenoma.

The treatment methods include administering the compounds of the present invention, e.g., any of 1.1-1.56, in free or salt form, together with other therapeutic compounds to treat hyperproliferative diseases, especially cancers of the brain or central nervous system, including astrocytoma, medulloblastoma, oligdendroglioma, glioblastoma, glioma, ependymoma, meningioma, sarcoma, germ cell tumor, pinealoma, craniopharyngioma, and pituitary adenoma.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

In addition to their use in therapeutic medicine, the compounds of formula (I) e.g., any of 1.1-1.56, in free or pharmaceutically acceptable salt forms are also useful as pharmacological tools in the development and standardisation of in vitro and in vivo test systems for the evaluation of the effects of dysfunctional expression or activity of kinases such as the c-Abl, BCR-Abl, ARG, c-Src, c-Kit, FAK, Trk, EGFR, VEGFR, Tie-2, c-Met, FGFR-1, Flt-1, Her-2, c-Raf, PDGFR, PDGFR-beta, MAPK, PKA, PKC, PKCα, PKCδ, CDK5, GSK-3, or JNK, especially over-expression or over-activity of kinases in CNS cells, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:
(i) temperatures are given in degrees Celsius (° C.); operations were carried out at room or ambient temperature ("rt") were at a temperature in the range of 18-25° C.;
(ii) organic solutions were dried over anhydrous sodium sulphate; evaporation of solvent is carried out using a rotary evaporator under reduced pressure (600-4000 Pascals; 4.5-30 mmHg) with a bath temperature of up to 60° C.;
(iii) in general, the course of reactions is followed by TLC and reaction times are given for illustration only;
(iv) final products had satisfactory proton nuclear magnetic resonance (NMR) spectra and/or mass spectral data;

(v) yields are given for illustration only and are not necessarily those which can be obtained by diligent process development; preparations were repeated if more material is required;
(vii) when given, NMR data is in the form of delta values for major diagnostic protons, given in parts per million (ppm) relative to tetramethylsilane (TMS) as an internal standard, determined at 400 MHz using perdeuterio dimethyl sulphoxide (DMSO-$d_6$) as solvent unless otherwise indicated;
(vii) chemical symbols have their usual meanings; SI units and symbols are used;
(viii) solvent ratios are given in volume:volume (v/v) terms; and
(ix) mass spectra were run with an electron energy of 70 electron volts in the chemical ionization (CI) mode using a direct exposure probe; where indicated ionization is effected by electron impact (EI), fast atom bombardment (FAB) or electrospray (ESP); values for m/z are given; generally, only ions which indicate the parent mass are reported; and unless otherwise stated, the mass ion quoted is [MH]$^+$;
(x) where a synthesis is described as being analogous to that described in a previous example the amounts used are the millimolar ratio equivalents to those used in the previous example;
(xi) the following abbreviations have been used:

| | |
|---|---|
| $Cs_2CO_3$ | cesium carbonate; |
| HOBt | 1H-benzo[d][1,2,3]triazol-1-ol; |
| HPLC | high performance liquid chromatography; |
| MeOH | methanol; |
| $NaHCO_3$ | sodium bicarbonate; |
| BOP | benzotriazol-1-yloxytris(dimethylamino)phosphonium hexafluorophosphate; |
| THF | tetrahydrofuran; |
| DMF | N,N-dimethylformamide; |
| EtOAc | ethyl acetate; |
| DIEA | N,N-diisopropylethylamine; |
| DCM | dichloromethane; |
| DMSO | dimethylsulphoxide; and |
| MeCN | acetonitrile; |

(xii) "ISCO" refers to normal phase flash column chromatography using 12 g and 40 g pre-packed silica gel cartridges used according to the manufacturer's instructions obtained from ISCO, Inc, 4700 superior street Lincoln, Nebr., U.S.A.

Example 1

N-(3-(4-(3-Chloro-2-fluorophenyl)pyrimidin-2-ylamino)phenyl)-4-(piperidin-1-ylmethyl)benzamide

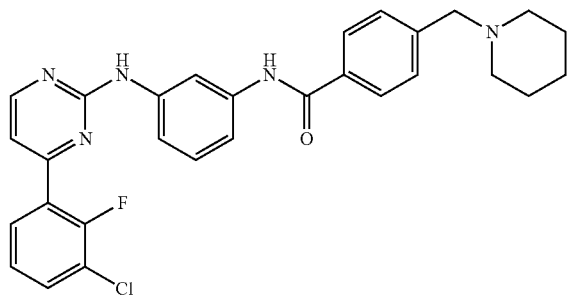

(a) N-(3-Bromophenyl)-4-(piperidin-1-ylmethyl)benzamide

DIEA (433 μL, 2.49 mmol) was added into a suspension of 3-bromobenzenamine (90.3 μL, 0.829 mmol), 4-(piperidin-1-ylmethyl)benzoic acid (200 mg, 0.912 mmol), BOP (477 mg, 1.08 mmol) in DMF (2 mL). The reaction mixture was stirred at room temperature under argon atmosphere overnight. The reaction mixture was loaded onto a 5 g silica loading cartridge. After solvent in the cartridge was dried out under vacuum, the cartridge was put on the ICSO system for purification (yield: 80%). MS (ESI$^+$) m/z 373.0 [M+H]$^+$.

(b) N-(3-(4-(3-Chloro-2-fluorophenyl)pyrimidin-2-ylamino)phenyl)-4-(piperidin-1-ylmethyl)benzamide A mixture of N-(3-bromophenyl)-4-(piperidin-1-ylmethyl)benzamide (20 mg, 0.054 mmol) and 4-(3-chloro-2-fluorophenyl)pyrimidin-2-amine (18 mg, 0.080 mmol), KOBu$^t$ (12 mg, 0.11 mmol), Pd$_2$(dba)$_3$ (2.5 mg, 0.027 mmol) and Xantphos (2.5 mg, 0.043 mmol) in a microwave reaction vessel was suspended in 0.6 mL of toluene. The reaction mixture was heated in a microwave at 150° C. for 1 h. After cooling, the mixture was diluted with DMF, and then filtered with a 0.45 μm microfilter. The obtained filtrate was separated by a semi-preparative HPLC. Collected product fraction was lyophilized to give pure product as a while powder. MS (ESI$^+$) m/z 516.2 [M+H]$^+$.

Example 2

4-(Piperidin-1-ylmethyl)-N-(3-(4-(3-(trifluoromethyl)phenyl)pyrimidin-2-ylamino)phenyl)benzamide

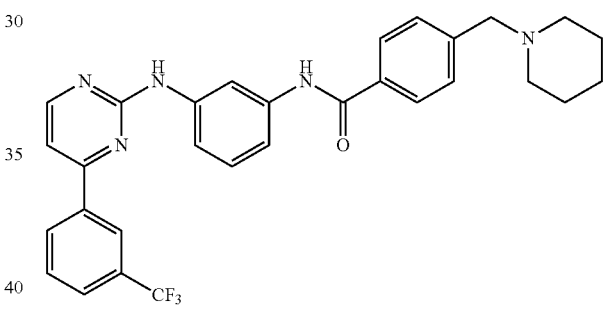

The synthesis method is analogous to EXAMPLE 1 wherein 4-(3-(trifluoromethyl)phenyl)pyrimidin-2-amine was added in step (b) instead of 4-(3-chloro-2-fluorophenyl)pyrimidin-2-amine. MS (ESI$^+$) m/z 532.1 [M+H]$^+$.

Example 3

4-(Piperidin-1-ylmethyl)-N-(3-(4-(trifluoromethyl)pyrimidin-2-ylamino)phenyl)benzamide

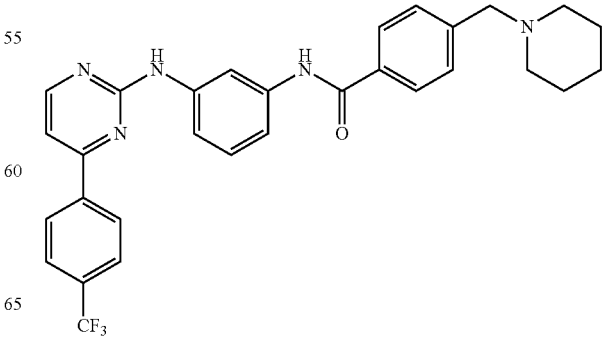

The synthesis method is analogous to EXAMPLE 1 wherein 4-(trifluoromethyl)pyrimidin-2-amine was added in step (b) instead of 4-(3-chloro-2-fluorophenyl)pyrimidin-2-amine. MS (ESI$^+$) m/z 456.2 [M+H]$^+$.

Example 4

4-Methyl-N-(4-((4-methylpiperazin-1-yl)methyl)phenyl)-3-(4-phenylpyrimidin-2-ylamino)benzamide

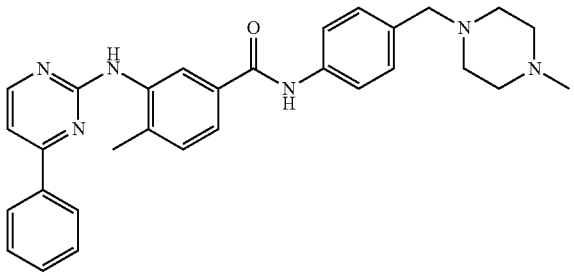

(a) Methyl 4-methyl-3-(4-phenylpyrimidin-2-ylamino)benzoate

A mixture of 4-phenylpyrimidin-2-amine (100 mg, 0.58 mmol) and methyl 3-bromo-4-methylbenzoate (111 mg, 0.48 mmol), Cs$_2$CO$_3$ (221 mg, 0.68 mmol), Pd$_2$(dba)$_3$ (22 mg, 0.024 mmol) and Xantphos (22 mg, 0.039 mmol) in a microwave reaction vessel was suspended in 5 mL of toluene. The reaction mixture was heated in a microwave at 130° C. for 30 min, and then at 180° C. for 30 min. After cooling, the mixture was purified by ISCO system to give 80 mg of product (yield: 43%). MS (ESI$^+$) m/z 320.1 [M+H]$^+$.

(b) 3-Bromo-4-methylbenzoic acid 1 mL of 2.5N NaOH was added into a solution of methyl 4-methyl-3-(4-phenylpyrimidin-2-ylamino)benzoate (80 mg, 0.25 mmol) in methanol (1 mL). The reaction mixture was stirred at 40° C. for 1 h. Solvent was removed under reduced pressure. The obtained residue was treated with 5 mL of water, and then adjusted to pH=4. The resulting suspension was extracted with dichloromethane three times. Organic phase was combined and evaporated to remove solvent to give 40 mg of product as white powder (yield: 53%). MS (ESI$^+$) m/z 306.2 [M+H]$^+$.

(c) 4-Methyl-N-(4-((4-methylpiperazin-1-yl)methyl)phenyl)-3-(4-phenylpyrimidin-2-ylamino)benzamide DIEA (50 µL, 0.204 mmol) was added into a solution of 3-bromo-4-methylbenzoic acid (15 µmg, 0.049 mmol), 4-((4-methylpiperazin-1-yl)methyl)benzenamine (9 mg, 0.04 mmol), BOP (25 mg, 0.057 mmol) in DMF. The reaction mixture was stirred at rt under argon atmosphere overnight. The reaction mixture was then purified by a semi-preparative HPLC to give pure product as white powder. MS (ESI$^+$) m/z 493.2 [M+H]$^+$.

Example 5

N-(3-(4-Phenylpyrimidin-2-ylamino)phenyl)-4-(piperidin-1-ylmethyl)benzamide

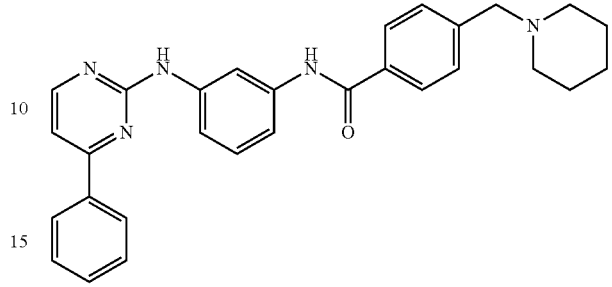

The synthesis method is analogous to EXAMPLE 1 wherein 4-phenylpyrimidin-2-amine was added in step (b) instead of 4-(3-chloro-2-fluorophenyl)pyrimidin-2-amine. MS (ESI$^+$) m/z 464.2 [M+H]$^+$.

Example 6

4-(Piperidin-1-ylmethyl)-N-(3-(4-p-tolylpyrimidin-2-ylamino)phenyl)benzamide

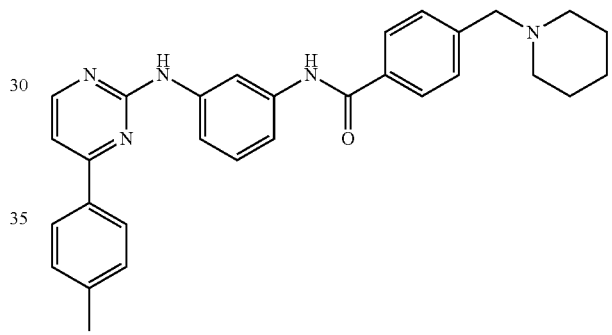

The synthesis method is analogous to EXAMPLE 1 wherein 4-p-tolylpyrimidin-2-amine was added in step (b) instead of 4-(3-chloro-2-fluorophenyl)pyrimidin-2-amine. MS (ESI$^+$) m/z 478.3 [M+H]$^+$.

Example 7

N-(3-(4-(4-Methoxyphenyl)pyrimidin-2-ylamino)phenyl)-4-(piperidin-1-ylmethyl)benzamide

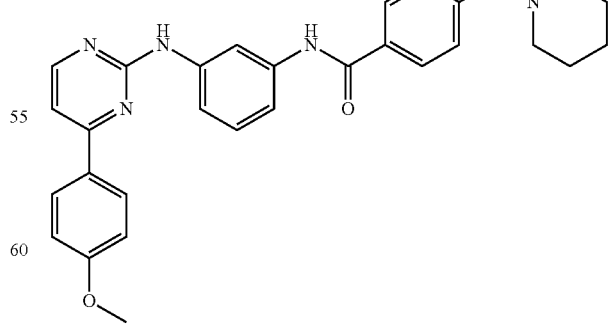

The synthesis method is analogous to EXAMPLE 1 wherein 4-(4-methoxyphenyl)pyrimidin-2-amine was added in step (b) instead of 4-(3-chloro-2-fluorophenyl)pyrimidin-2-amine. MS (ESI$^+$) m/z 494.2 [M+H]$^+$.

Example 8

N-(3-(4-Phenyl-6-(trifluoromethyl)pyrimidin-2-ylamino)phenyl)-4-(piperidin-1-ylmethyl)benzamide

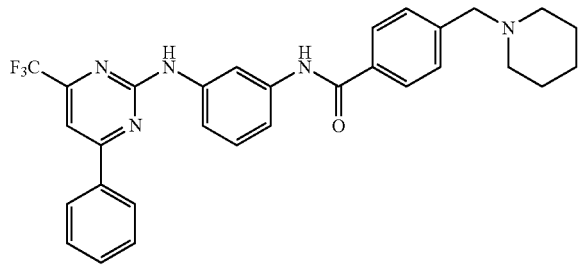 [SMILES: O=C(Nc1cccc(Nc2nc(-c3ccccc3)cc(C(F)(F)F)n2)c1)c1ccc(CN2CCCCC2)cc1]

The synthesis method is analogous to EXAMPLE 1 wherein 4-phenyl-6-(trifluoromethyl)pyrimidin-2-amine was added in step (b) instead of 4-(3-chloro-2-fluorophenyl)pyrimidin-2-amine. MS (ESI$^+$) m/z 494.2 [M+H]$^+$.

Example 9

4-Methyl-3-(4-phenylpyrimidin-2-ylamino)-N-(4-(2-(pyrrolidin-1-yl)ethyl)phenyl)benzamide

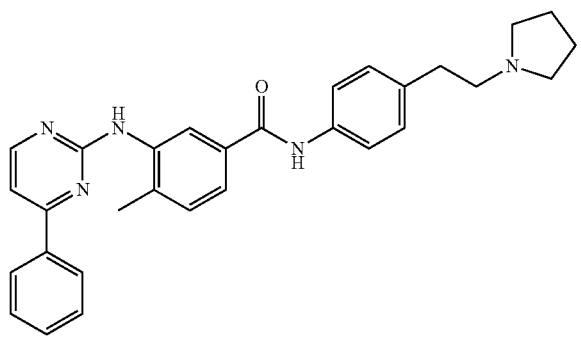 [SMILES: Cc1ccc(C(=O)Nc2ccc(CCN3CCCC3)cc2)cc1Nc1nccc(-c2ccccc2)n1]

The synthesis method is analogous to EXAMPLE 4 wherein 4-(2-(pyrrolidin-1-yl)ethyl)benzenamine was added in step (c) instead of 4-((4-methylpiperazin-1-yl)methyl)benzenamine. MS (ESI$^+$) m/z 478.1 [M+H]$^+$.

Example 10

4-Methyl-N-(4-(2-(pyrrolidin-1-yl)ethyl)phenyl)-3-(4-(3-(trifluoromethyl)phenyl)pyrimidin-2-ylamino)benzamide

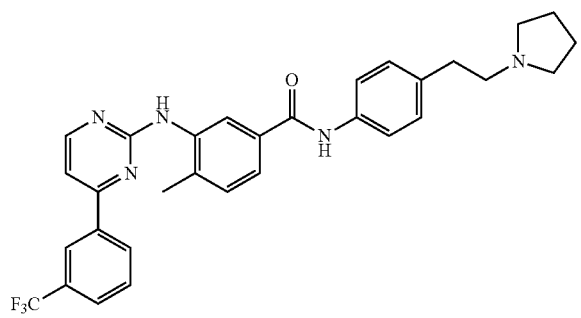 [SMILES: Cc1ccc(C(=O)Nc2ccc(CCN3CCCC3)cc2)cc1Nc1nccc(-c2cccc(C(F)(F)F)c2)n1]

(a) 3-Bromo-4-methyl-N-(4-(2-(pyrrolidin-1-yl)ethyl)phenyl)benzamide

DIEA (4734, 2.72 mmol) was added into a solution of 3-bromo-4-methylbenzoic acid (189 mL, 0.881 mmol), 4-(2-(pyrrolidin-1-yl)ethyl)benzenamine (140 mg, 0.734 mmol), BOP (487 mg, 1.01 mmol) in DMF. The reaction mixture was stirred at rt under argon atmosphere overnight. The reaction mixture was diluted with AcOEt, and then washed with 1N NaOH aqueous solution three times. Organic phase was dried with anhydrous Na$_2$SO$_4$, and then evaporated to remove organic solvents. The obtained residue was further dried under high vacuum overnight to give crude product, which was used directly for the next step synthesis without further purification. MS (ESI$^+$) m/z 387.0 [M+H]$^+$.

(b) 4-Methyl-N-(4-(2-(pyrrolidin-1-yl)ethyl)phenyl)-3-(4-(3-(trifluoromethyl)phenyl)pyrimidin-2-ylamino)benzamide A mixture of 3-bromo-4-methyl-N-(4-(2-(pyrrolidin-1-yl)ethyl)phenyl)benzamide (59 mg, 0.13 mmol) and 4-(3-(trifluoromethyl)phenyl)pyrimidin-2-amine (31 mg, 0.13 mmol), KOBu$^t$ (22 mg, 0.2 mmol), Pd$_2$(dba)$_3$ (4.6 mg, 0.005 mmol) and Xantphos (4.6 mg, 0.008 mmol) in a microwave reaction vessel was suspended in 1 mL of THF. The reaction mixture was heated in a microwave at 150° C. for 90 min. After cooling, the mixture was diluted with DMF, and then filtered with a 0.45 μm microfilter. The obtained filtrate was separated by a semi-preparative HPLC. Collected product fraction was lyophilized to give pure product as a while powder. MS (ESI$^+$) m/z 546.1 [M+H]$^+$.

Example 11

4-Fluoro-N-(4-(2-(pyrrolidin-1-yl)ethyl)phenyl)-3-(4-(3-(trifluoromethyl)phenyl)pyrimidin-2-ylamino)benzamide

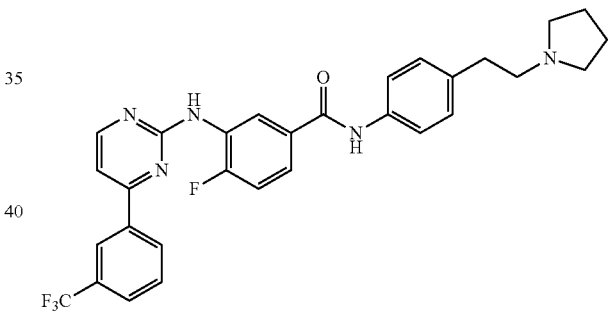

The synthesis method is analogous to EXAMPLE 10 wherein 3-bromo-4-fluorobenzoic acid was added in step (a) instead of 3-bromo-4-methylbenzoic acid. MS (ESI$^+$) m/z 550.0 [M+H]$^+$.

Example 12

4-Methyl-3-(4-phenylpyridin-2-ylamino)-N-(4-(2-(pyrrolidin-1-yl)ethyl)phenyl)benzamide

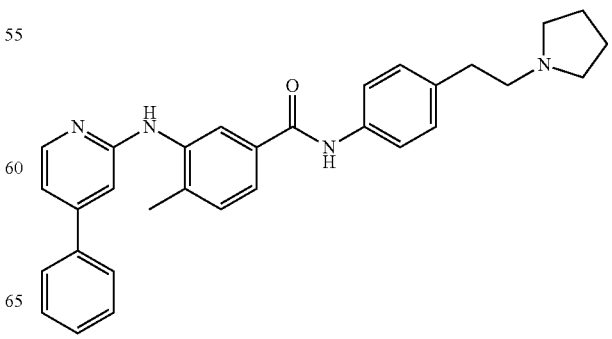

The synthesis method is analogous to EXAMPLE 10 wherein 4-phenylpyridin-2-amine was added in step (b) instead of 4-(3-(trifluoromethyl)phenyl)pyrimidin-2-amine. MS (ESI⁺) m/z 477.1 [M+H]⁺.

Example 13

4-Methoxy-N-(4-(2-(pyrrolidin-1-yl)ethyl)phenyl)-3-(4-(3-(trifluoromethyl)phenyl)pyrimidin-2-ylamino)benzamide

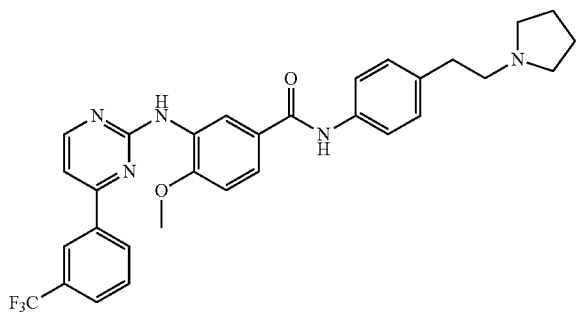 [SMILES: COc1ccc(C(=O)Nc2ccc(CCN3CCCC3)cc2)cc1Nc1nccc(-c2cccc(C(F)(F)F)c2)n1]

The synthesis method is analogous to EXAMPLE 10 wherein 3-bromo-4-methoxybenzoic acid was added in step (a) instead of 3-bromo-4-methylbenzoic acid. MS (ESI⁺) m/z 562.1 [M+H]⁺.

Example 14

N-(4-(2-(Pyrrolidin-1-yl)ethyl)phenyl)-5-(4-(3-(trifluoromethyl)phenyl)pyrimidin-2-ylamino)-2,3-dihydrobenzofuran-7-carboxamide

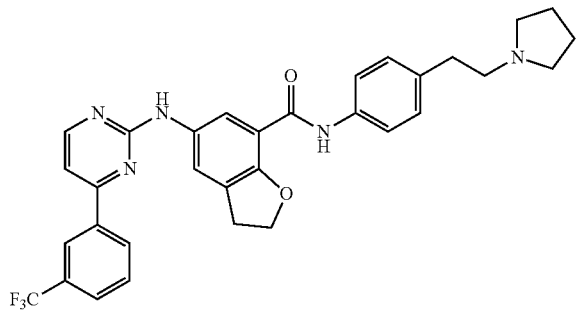 [SMILES: O=C(Nc1ccc(CCN2CCCC2)cc1)c1cc(Nc2nccc(-c3cccc(C(F)(F)F)c3)n2)cc2c1OCC2]

The synthesis method is analogous to EXAMPLE 10 wherein 5-bromo-2,3-dihydrobenzofuran-7-carboxylic acid was added in step (a) instead of 3-bromo-4-methylbenzoic acid. MS (ESI⁺) m/z 574.1 [M+H]⁺.

Example 15

3-(4-Ethylpyridin-2-ylamino)-4-methyl-N-(4-(2-(pyrrolidin-1-yl)ethyl)phenyl)benzamide

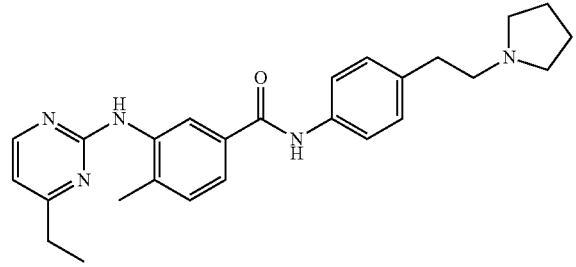 [SMILES: CCc1ccnc(Nc2cc(C(=O)Nc3ccc(CCN4CCCC4)cc3)ccc2C)n1]

The synthesis method is analogous to EXAMPLE 10 wherein 4-ethylpyridin-2-amine was added in step (b) instead of 4-(3-(trifluoromethyl)phenyl)pyrimidin-2-amine. MS (ESI⁺) m/z 429.0 [M+H]⁺.

Example 16

N2a Cell Assay

Evaluation of Amyloid Beta (Aβ) Production in N2a Cells. The influence of compounds on Aβ production in N2a cells is carried out as described by Netzer, W. J., Dou, F., Cai, D., Veach, D., Jean, S., Li, Y., Bornmann, W. G., Clarkson, B., Xu, H., and Greengard, P. (2003) *Proc Natl Acad Sci USA* 100, 12444-12449. The exemplified Compounds of the Invention inhibit amyloid beta by at least 50% at concentrations 10 micromolar over 24 hours.

Example 17

Mouse Brain/Plasma Distribution Assay for the Evaluation of Tissue Levels of Test Compounds Compounds are administered subcutaneously to C57bl/6 black mice as a single injection of 1 mg using a 10 mM DMSO solution. After 2 or 4 hours, the mice are sacrificed. Trunk blood is collected into tubes with potassium-EDTA as anticoagulant and centrifuged at 5000×g for 10 min. The upper plasma phase is decanted from cellular components. Whole brain is sonicated with 20 mM Tris-HCl, 135 mM NaCl, pH 7.4 buffer, giving at 200 mg/mL (w/v) homogenate. Brain homogenate or plasma is extracted with 2 volumes of acetonitrile and clarified by centrifugation at 15,000×g for 20 min. Extracts are separated by HPLC using a Waters Alliance 2695 separations module with a Sunfire™ C18 column (3.5 micron, 2.1×50 mm) and a gradient of methanol over 15 min in a mobile phase of 0.1% formic acid. The separation is monitored by a Micromass Quattro Micro triple-quadrupole mass-spectrometric detector. Compound standardization is performed by methods analogous to those previously reported, e.g., by Zhao, M., et al. (2005) *J Chromatogr B Analyt Technol Biomed Life Sci* 819, 73-80; and Appels, N. M et al. (2005) *Rapid Commun Mass Spectrom* 19, 2187-2192.

Brain concentration=measured−2% of plasma

B/P ratio=brain concentration/plasma concentration

Exemplified Compounds of the Invention have a B/P ratio in this assay at four hours post-administration of greater than 0.6, while having a brain concentration of greater than 0.3 μM at four hours post administration compared to the brain concentration of imatinib at four hours post-administration of less than 0.1 μM, demonstrating a substantially higher level of penetration and accumulation in the brain for the Compounds of the Invention.

What is claimed:

1. A method for the treatment of a disease or disorder, wherein the disease or disorder is characterized as a neurodegenerative disease characterized by the accumulation of abnormal protein aggregates in the brain, or a hyperproliferative disease of the brain or central nervous system, comprising administering to a subject a pharmaceutically effective amount of a compound according formula (I):

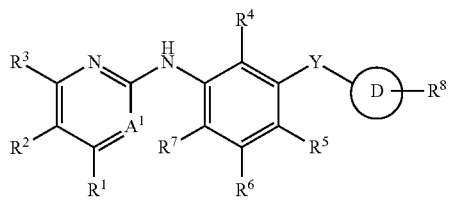

(I)

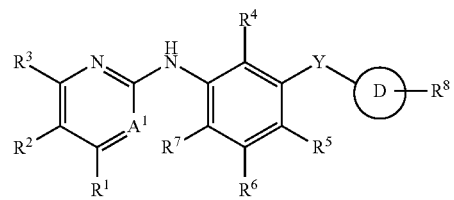

(I)

wherein:

A¹ is CH or N;

R¹ is $C_{1-6}$ alkyl, $C_{1-6}$cycloalkyl, or aryl optionally substituted with alkyl, haloalkyl, alkyloxy or halo group;

$R^2$, $R^3$, $R^4$, $R^5$, $R^6$ and $R^7$ are independently hydrogen, halo, $C_{1-4}$alkyl, $C_{1-4}$alkyloxy, or trifluoromethyl;

or $R^5$ and $R^6$, together with carbon atoms to which they are attached, form a 5 or 6 member hetcyclic ring;

Y is —NHCO—, —CONH—, —NHSO₂—, —NH-CONH—, or —NHCH₂—;

D is a 5 or 6 member aryl, hetaryl or hetcyclic ring having at least one N, S, or O ring atom, or a C ring atom forming an oxo (C=O) moiety; provided that D is not a substituted phenyl group if $A^1$=N and $R^2$=$R^3$=$R^4$=$R^5$=$R^6$=H and $R^7$=CH₃ and Y=NHCO; and $R^8$ is $C_{0-6}$alkyl, $C_{3-7}$cycloalkyl, aryl, hetaryl, aryl($C_{1-4}$ alkyl)-, hetcyclyl($C_{0-4}$alkyl)-, or —$C_{0-6}$alkyl-N($C_{0-6}$ alkyl)($C_{0-6}$alkyl), optionally substituted with $C_{1-6}$alkyl;

in a free or pharmaceutically acceptable salt form, to a patient in need thereof.

2. The method of treatment according to claim 1, wherein the neurodegenerative characterized by the accumulation of abnormal protein aggregates in the brain is selected from the group consisting of: Alzheimer's disease, progressive supranuclear palsy, Down Syndrome, dementia, amyloid neuropathies, nerve and brain trauma, vascular amyloidosis, cerebral hemorrhage with amyloidosis, Parkinson's disease, Huntington's disease, prion disease, and neurological or neurodegenerative disorders related to the abnormal expression or accumulation of tau or amyloid proteins.

3. The method of treatment according to claim 2, wherein the abnormal protein aggregates are selected from the group consisting of: amyloid plaques, neurofibrillary tangles, or precipitates of tau or amyloid proteins.

4. The method of treatment according to claim 1, wherein the hyperproliferative disease of the brain or central nervous system is selected from the group consisting of: astrocytoma, medulloblastoma, oligdendroglioma, glioblastoma, glioma, ependymoma, meningioma, sarcoma, germ cell tumor, pinealoma, craniopharyngioma, and pituitary adenoma.

5. The method of treatment according to claim 2, wherein the compound according to formula I is administered in conjunction with other therapeutic compounds.

6. The method of treatment according to claim 4, wherein the compound according to formula I is administered in conjunction with other therapeutic compounds.

7. A method for the treatment of a disease or disorder, wherein the disease or disorder is characterized by dysfunctional kinase expression or kinase activity, comprising administering to a subject a pharmaceutically effective amount of a compound according formula (I):

wherein:

A¹ is CH or N;

R¹ is $C_{1-6}$ alkyl, $C_{1-6}$cycloalkyl, or aryl optionally substituted with alkyl, haloalkyl, alkyloxy or halo group;

$R^2$, $R^3$, $R^4$, $R^5$, $R^6$ and $R^7$ are independently hydrogen, halo, $C_{1-4}$alkyl, $C_{1-4}$alkyloxy, or trifluoromethyl;

or $R^5$ and $R^6$, together with carbon atoms to which they are attached, form a 5 or 6 member hetcyclic ring;

Y is —NHCO—, —CONH—, —NHSO₂—, —NH-CONH—, or —NHCH₂—;

D is a 5 or 6 member aryl, hetaryl or hetcyclic ring having at least one N, S, or O ring atom, or a C ring atom forming an oxo (C=O) moiety; provided that D is not a substituted phenyl group if $A^1$=N and $R^2$=$R^3$=$R^4$=$R^5$=$R^6$=H and $R^7$=CH₃ and Y=NHCO; and $R^8$ is $C_{0-6}$alkyl, $C_{3-7}$cycloalkyl, aryl, hetaryl, aryl($C_{1-4}$ alkyl)-, hetcyclyl($C_{0-4}$alkyl)-, or —$C_{0-6}$alkyl-N($C_{0-6}$ alkyl)($C_{0-6}$alkyl), optionally substituted with $C_{1-6}$alkyl;

in a free or pharmaceutically acceptable salt form, to a patient in need thereof.

8. The method of treatment according to claim 7, wherein the disease or disorder characterized by dysfunctional kinase expression or kinase activity is selected from the kinases consisting of: c-Abl, BCR-Abl, ARG, c-Src, c-Kit, FAK, Trk, EGFR, VEGFR, Tie-2, c-Met, FGFR-1, Flt-1, Her-2, c-Raf, PDGFR, PDGFR-beta, MAPK, PKA, PKC, PKCα, PCKδ, CDK5, GSK-3, and JNK.

9. The method of treatment according to claim 1, wherein the compound according to formula (I) is selected from the group consisting of:

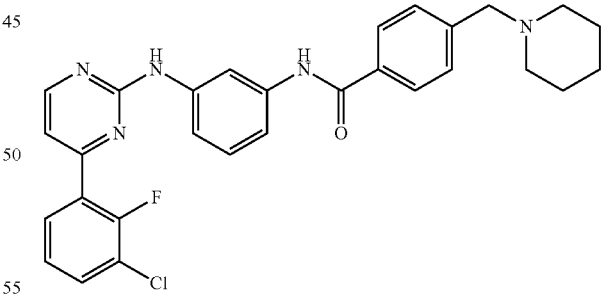

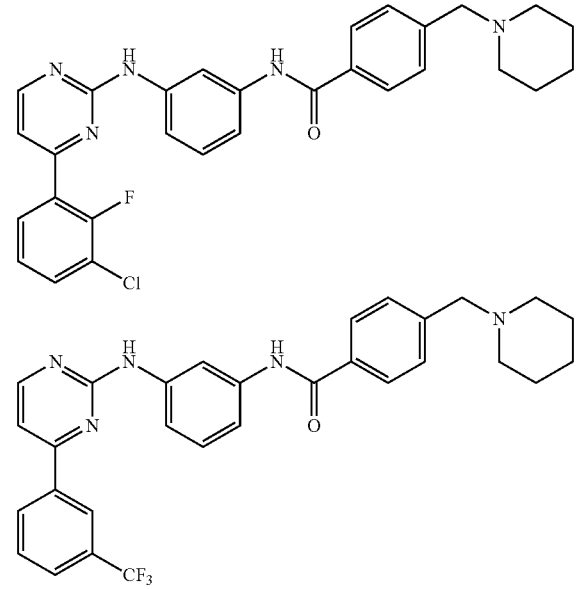

-continued
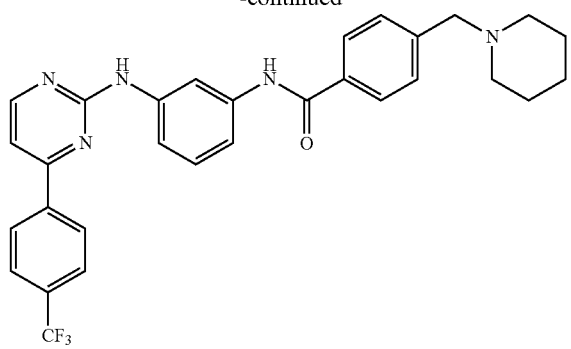
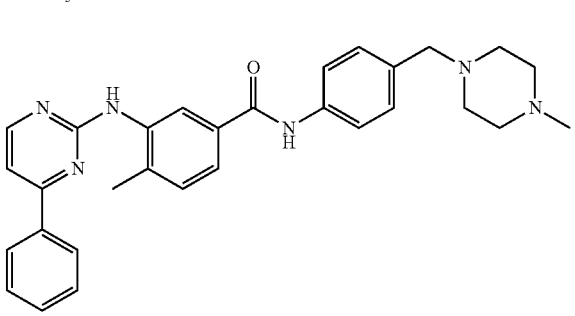
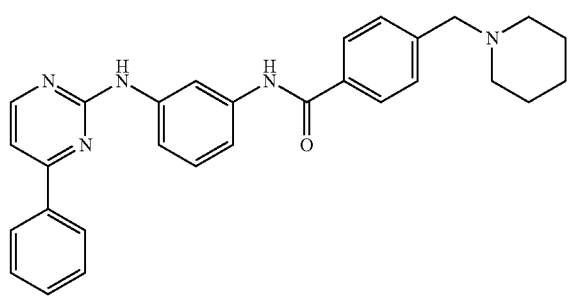
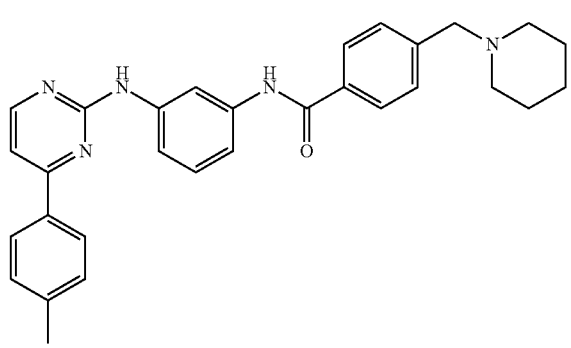
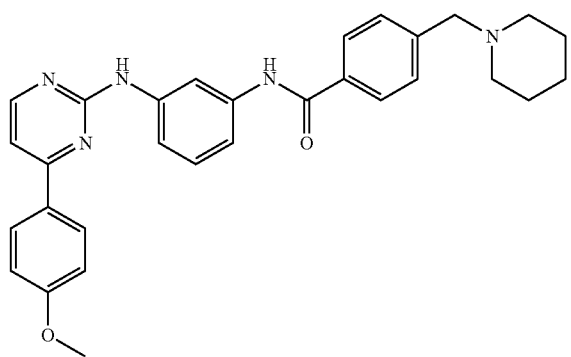
-continued
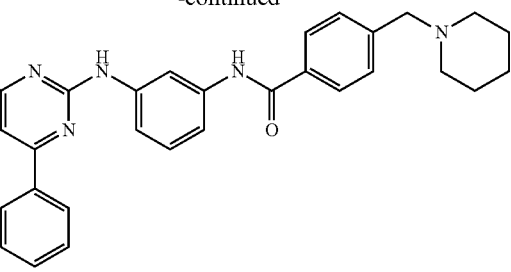
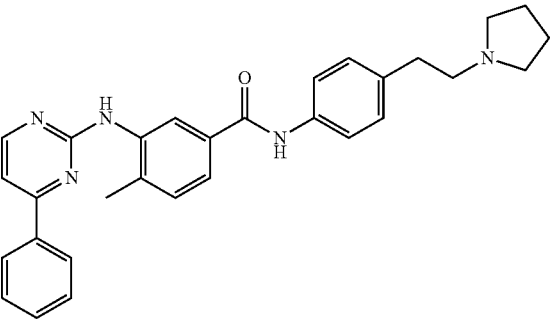
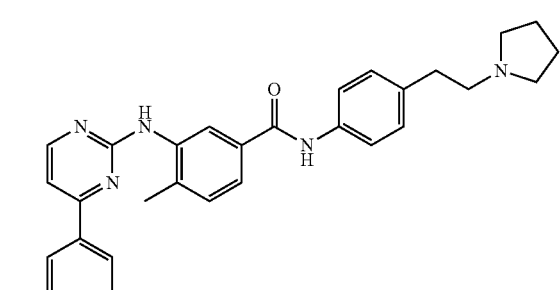
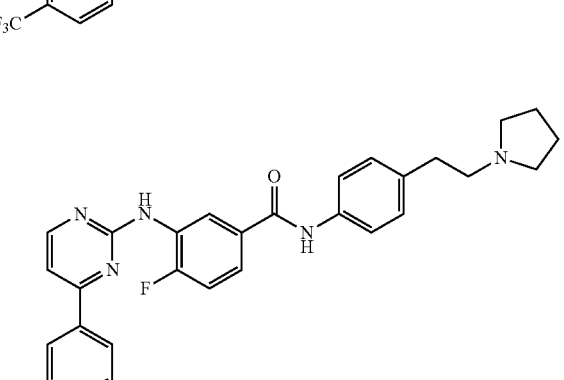
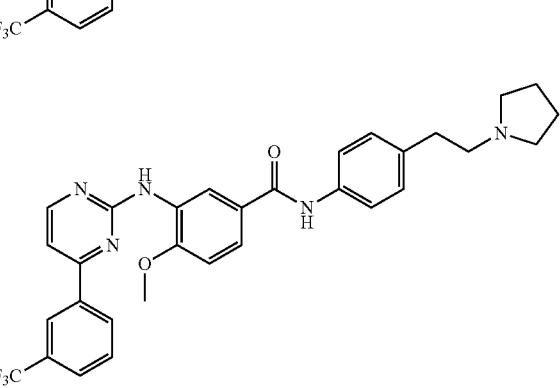

-continued

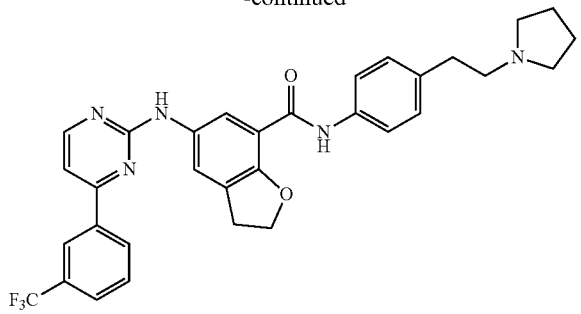

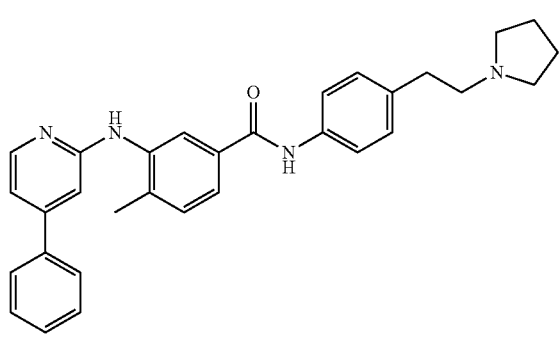

in free or pharmaceutically acceptable salt form.

10. The method of treatment according to claim 1, wherein the compound according to formula (I) is:

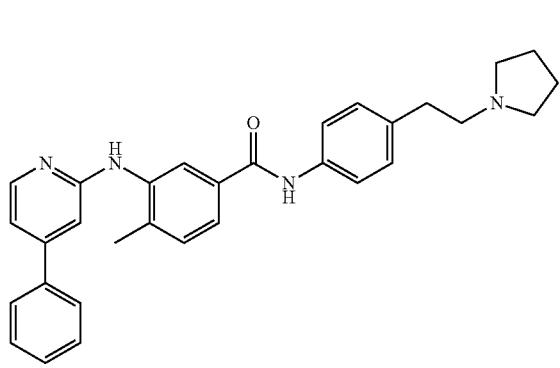 [SMILES: Cc1ccc(C(=O)Nc2ccc(CCN3CCCC3)cc2)cc1Nc1cc(-c2ccccc2)ccn1]

in free or pharmaceutically acceptable salt form.

11. The method of treatment according to claim 1, wherein the compound according to formula (I) is:

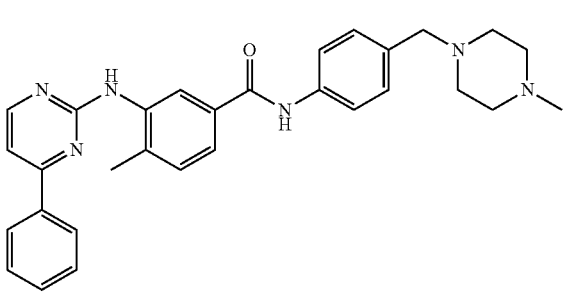 [SMILES: Cc1ccc(C(=O)Nc2ccc(CN3CCN(C)CC3)cc2)cc1Nc1nccc(-c2ccccc2)n1]

in free or pharmaceutically acceptable salt form.

12. The method of treatment according to claim 1, wherein the compound according to formula (I) is:

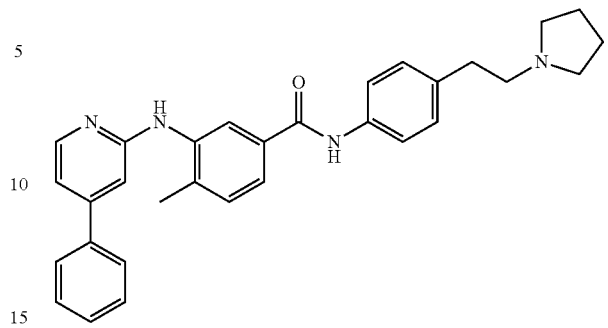

in free or pharmaceutically acceptable salt form.

13. The method of treatment according to claim 7, wherein the compound according to formula (I) is selected from the group consisting of:

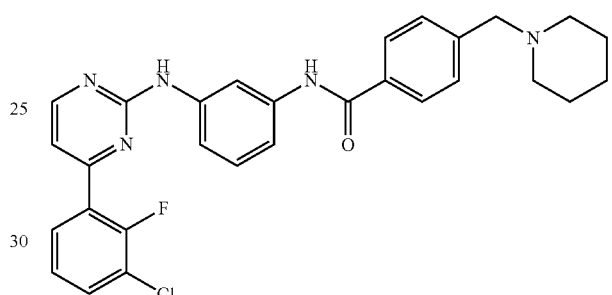

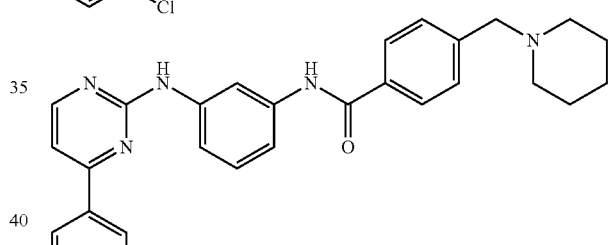

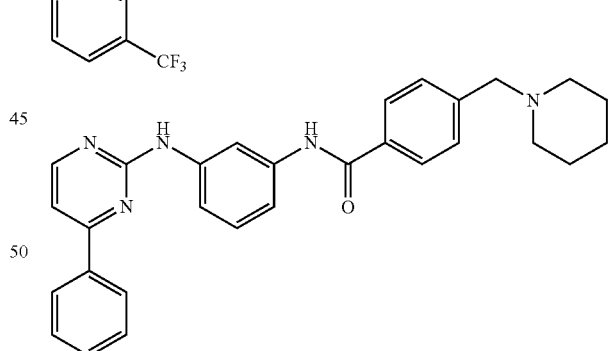

-continued
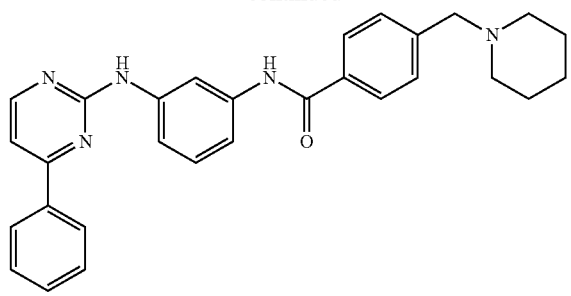
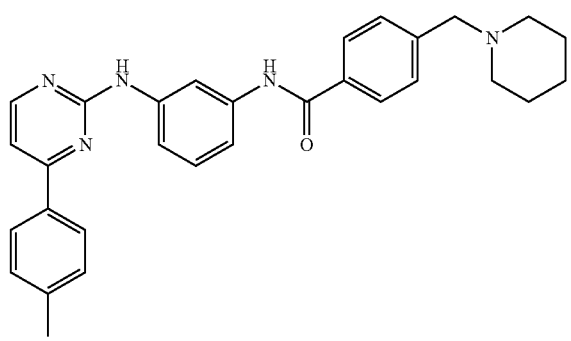
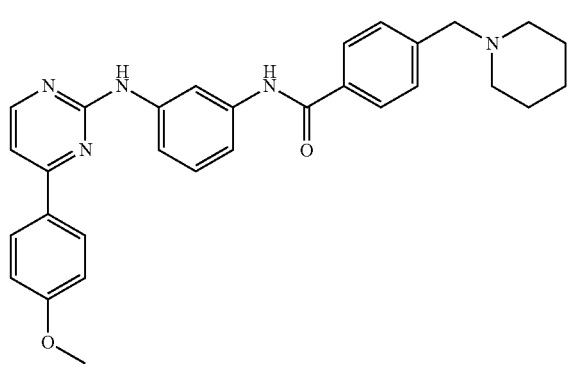
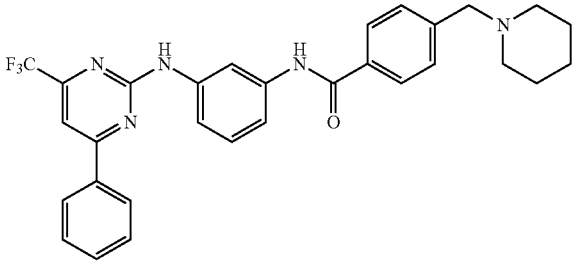
-continued
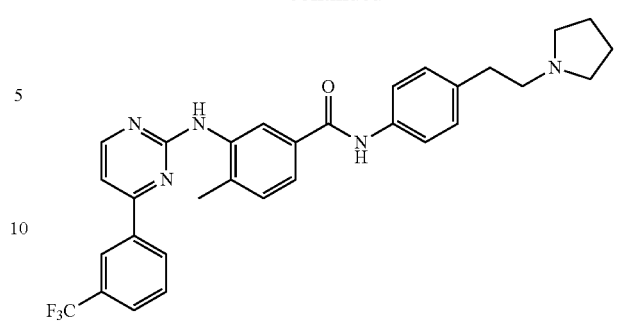
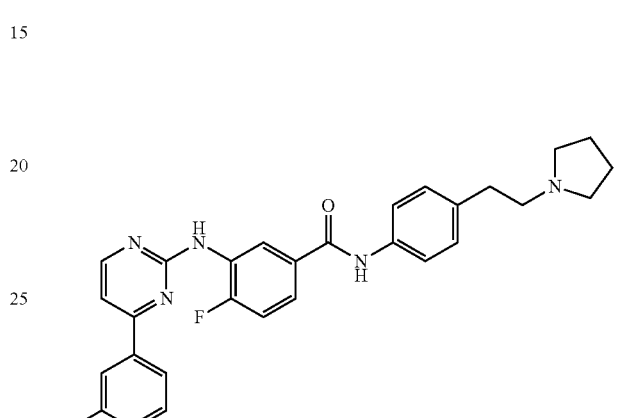
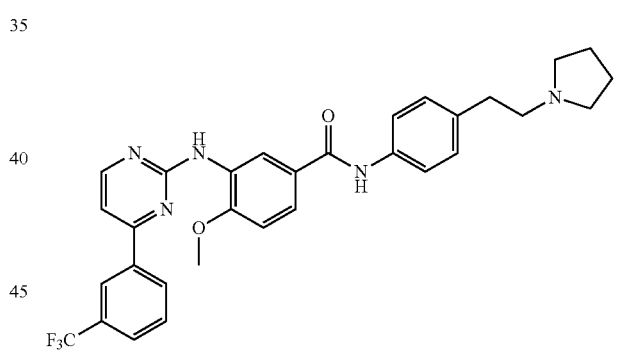
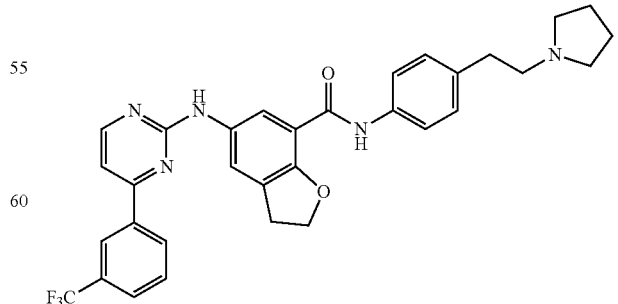
and

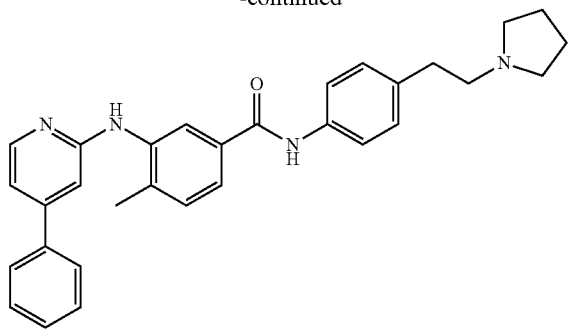

in free or pharmaceutically acceptable salt form.

14. The method of treatment according to claim 7, wherein the compound according to formula (I) is: in free or pharmaceutically acceptable salt form

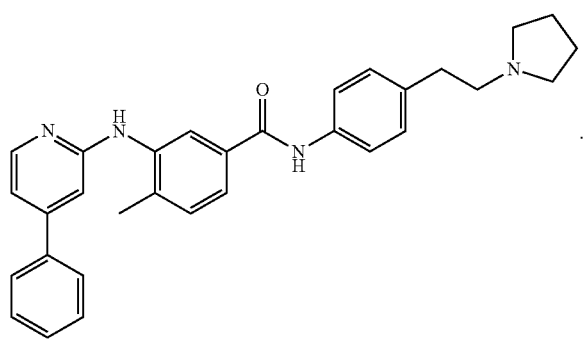

15. The method of treatment according to claim 7, wherein the compound according to formula (I) is: in free or pharmaceutically acceptable salt form

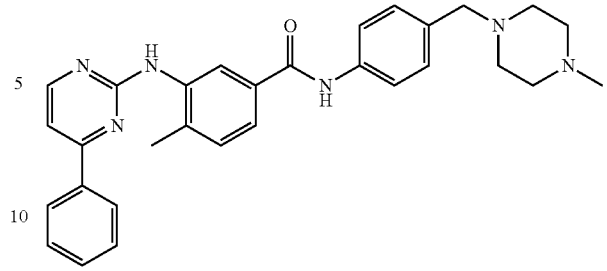

16. The method of treatment according to claim 7, wherein the compound according to formula (I) is: in free or pharmaceutically acceptable salt form

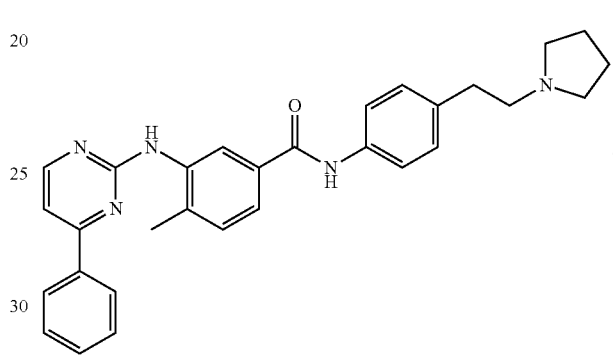

* * * * *